US008497382B2

(12) United States Patent
Ando

(10) Patent No.: US 8,497,382 B2
(45) Date of Patent: Jul. 30, 2013

(54) CARBOXYLIC ACID DERIVATIVE CONTAINING THIAZOLE RING AND PHARMACEUTICAL USE THEREOF

(75) Inventor: Naoko Ando, Osaka (JP)

(73) Assignee: Mitsubishi Tanabe Pharma Corporation, Osaka-Shi (JP)

(*) Notice: Subject to any disclaimer, the term of this patent is extended or adjusted under 35 U.S.C. 154(b) by 0 days.

(21) Appl. No.: 13/132,292

(22) PCT Filed: Dec. 1, 2009

(86) PCT No.: PCT/JP2009/070185
§ 371 (c)(1),
(2), (4) Date: Feb. 22, 2013

(87) PCT Pub. No.: WO2010/064633
PCT Pub. Date: Jun. 10, 2010

(65) Prior Publication Data
US 2011/0237630 A1 Sep. 29, 2011

(30) Foreign Application Priority Data
Dec. 1, 2008 (JP) .................. 2008-306803

(51) Int. Cl.
*A61K 31/426* (2006.01)
*C07D 277/36* (2006.01)

(52) U.S. Cl.
USPC ........................... 548/187; 514/369

(58) Field of Classification Search
USPC ..................................... 548/187
See application file for complete search history.

(56) References Cited

U.S. PATENT DOCUMENTS

| 6,306,854 B1 | 10/2001 | Brown et al. |
| 7,157,479 B2 | 1/2007 | Gellibert |
| 8,148,389 B2 | 4/2012 | Nakamura et al. |
| 2004/0097739 A1 | 5/2004 | Sakuma et al. |
| 2005/0054674 A1 | 3/2005 | Sakuma et al. |
| 2006/0160868 A1 | 7/2006 | Majka et al. |
| 2008/0167307 A1 | 7/2008 | Tozawa et al. |

FOREIGN PATENT DOCUMENTS

| CN | 1633421 A | 6/2005 |
| JP | 2002-527496 A | 8/2002 |
| JP | 2008-527021 A | 7/2008 |
| WO | 02/14291 A1 | 2/2002 |
| WO | 02/096895 A1 | 12/2002 |
| WO | 03/016291 A1 | 2/2003 |
| WO | WO 2006/049232 A1 | 5/2006 |
| WO | 2007/061094 A1 | 5/2007 |
| WO | WO 2007/126043 A1 | 11/2007 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*
Curtis et al., The Journal of the American Board of Family Practice, vol. 18, pp. 37-43, (2005).*
International Search Report, dated Jan. 26, 2010 in PCT/JP2009/070185.
Japanese Office Action dated Mar. 12, 2013 for Japanese Application No. 2010-541324, document in Japanese.
Chinese Office Action dated Apr. 17, 2013 for Chinese Application No. 200980155873.7 with English language translation.
Jing Danqing et al., Chinese Drug Application and Monitoring, vol. 4, No. 4, pp. 46-49 (2007).
Peter J. Brown, et al., Bioorganic & Medicinal Chemistry Letters, vol. 11, No. 9, pp. 1225-1227 (2001).

* cited by examiner

*Primary Examiner* — Laura L. Stockton
(74) *Attorney, Agent, or Firm* — Birch, Stewart, Kolasch & Birch, LLP

(57) ABSTRACT

A compound represented by the formula (I)

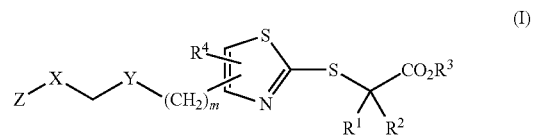

wherein $R^1$ and $R^2$ are each a hydrogen atom, an alkyl group and the like, $R^3$ is a hydrogen atom, an alkyl group and the like, $R^4$ is a hydrogen atom, an alkyl group and the like, m is an integer of 0 to 3, X is a bond, an oxygen atom or a sulfur atom, Y is a carbonyl group, a hydroxymethylene group and the like, and Z is a halogen atom, an alkyl group, an aryl group, a heteroaryl group and the like, or a pharmaceutically acceptable salt thereof has a superior PPARα agonist action and a lipid-lowering action, and is useful as a prophylactic or therapeutic drug for hyperlipidemia and the like.

8 Claims, No Drawings

CARBOXYLIC ACID DERIVATIVE CONTAINING THIAZOLE RING AND PHARMACEUTICAL USE THEREOF

CROSS-REFERENCE TO RELATED APPLICATIONS

The present application is a national phase under 35 U.S.C. §371 of PCT International Application No. PCT/JP2009/070185 which has an International filing date of Dec. 1, 2009, which claims priority of Application No. 2008-306803 filed in Japan on Dec. 1, 2008 under 35 U.S.C. §119.

TECHNICAL FIELD

The present invention relates to a novel carboxylic acid derivative containing a thiazole ring and a pharmaceutical agent containing the derivative as an active ingredient.

BACKGROUND ART

Peroxisome proliferator-activated receptor (PPAR) is a nuclear receptor cloned in 1990 as a receptor responsive to peroxisome proliferator, forms a heterodimer with other nuclear receptor, retinoid X receptor (RXR), and activates various target genes as a transcription factor. PPAR comprises three kinds of subtypes (PPARα, β(δ), γ), and it has been clarified that fibrate, which is a therapeutic drug for hyperlipidemia, acts as a ligand for PPARα, and a thiazolidine derivative, which is an insulin sensitizer, acts as a ligand for PPARγ.

Fibrate is a pharmaceutical agent widely used as a therapeutic drug for hyperlipidemia, and clofibrate, aluminum clofibrate, simfibrate, clinofibrate and the like have been heretofore used. At present, bezafibrate (Bezatol SR (registered trademark), Bezalip (registered trademark)) and fenofibrate (Lipidil (registered trade mark), Tricor (registered trade mark)), which are called the second generation, have been generally used.

Fibrate is known to regulate expression of genes (acyl CoA synthase, lipoprotein lipase, fatty acid transport protein and the like) relating to the metabolism of fatty acid and apolipoprotein (AI, AII, AV, CIII) genes involved in triglyceride (TG) and cholesterol metabolism, by activation of PPARα, decreases TG and LDL cholesterol and increases HDL cholesterol. Thus, fibrate is known to be highly effective as a therapeutic drug for hyperlipidemia.

However, since conventional fibrate shows a weak PPARα agonist activity ($EC_{50}$) of a μmol/L order (not less than 30 μmol/L), the dose needs to be as high as 200-1500 mg/day. In addition, various side effects such as digestive symptoms such as gastric distress, feeling of sickness and the like, skin symptoms such as anthema and the like, liver dysfunction and pancreatitis have been reported (foregoing from lipantil (registered trademark) package insert), and there is a room for further improvement as a pharmaceutical agent having a PPARα agonist action.

From the above, a pharmaceutical use as a compound superior in the pharmacological action based on PPARα activation (TG lowering action, LDL-C lowering action, HDL-C increasing action, anti-atherogenic action and the like) is expected by creating a compound capable of specifically activating PPARα than conventional fibrates.

Given such background, various carboxylic acid derivatives have been reported in recent years with regard to PPARα agonists. For example, patent document 1, non-patent document 1 and non-patent document 2 disclose (phenylthio)acetic acid derivatives, patent document 2 and non-patent document 3 disclose 3-phenylpropionic acid derivatives, patent document 3 and non-patent document 4 disclose phenoxyacetic acid derivatives, patent document 4 discloses phenoxyacetic acid derivatives, patent document 5 and non-patent document 5 disclose 2,2-dichloroalkanecarboxylic acid derivatives, patent document 6 discloses 1,3-dioxane-2-carboxylic acid derivatives, patent document 7 discloses phenoxyacetic acid derivatives, and patent document 8 discloses (1,3-thiazol-2-yl)-thioacetic acid derivatives.

DOCUMENT LIST

Patent Documents patent document 1: WO00/23407
patent document 2: WO00/75103
patent document 3: WO02/38553
patent document 4: WO02/28821
patent document 5: WO96/15784
patent document 6: WO01/90087
patent document 7: WO02/096894
patent document 8: WO2006/049232

Non-Patent Documents non-patent document 1: J. Med. Chem., 42, 3785 (1999)
non-patent document 2: Bioorg. Med. Chem. Lett., 11, 1225 (2001)
non-patent document 3: Bioorg. Med. Chem. Lett., 12, 333 (2002)
non-patent document 4: J. Med. Chem., 46, 5121 (2003)
non-patent document 5: Am. J. Physiol., 283 (3, Pt. 2), H949 (2002)

SUMMARY OF THE INVENTION

Problems to be Solved by the Invention

It is an object of the present invention to provide a compound having a PPARα agonist action, which is useful as a drug for the prophylaxis and/or treatment of hyperlipidemia, and a compound useful as an intermediate therefor.

Means of Solving the Problems

In an attempt to develop a drug useful as an agent for the prophylaxis and/or treatment of hyperlipidemia, the present inventors took note of the role of PPARα relating to the lipid metabolism and conducted intensive studies. As a result, a compound represented by the following formula (I) has a superior PPARα agonist action and a lipid-lowering action, and found a compound useful as a synthetic intermediate for the compound, which resulted in the completion of the present invention.

Accordingly, the present invention provides the following.
[1] A carboxylic acid derivative containing a thiazole ring represented by the following formula (I)

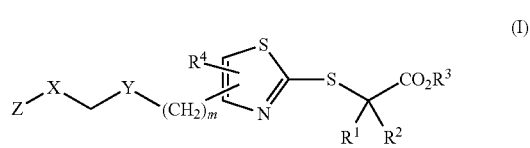

wherein

R¹ and R² are the same or different and each is a hydrogen atom or an alkyl group optionally having substituent(s), or R¹ and R² are bonded to each other to form a cycloalkyl group optionally having substituent(s);

R³ is a hydrogen atom or an alkyl group optionally having substituent(s);

R⁴ is a hydrogen atom, an alkyl group optionally having substituent(s) or an aryl group optionally having substituent(s);

m is an integer of 0 to 3;

X is a bond, an oxygen atom or a sulfur atom;

Y is a carbonyl group or a group represented by —CH(OR⁵)— wherein R⁵ is a hydrogen atom or an alkyl group optionally having substituent(s); and Z is
a halogen atom,
an alkyl group optionally having substituent(s),
a cycloalkyl group optionally having substituent(s),
an aryl group optionally having substituent(s),
an arylalkyl group optionally having substituent(s),
an arylalkenyl group optionally having substituent(s),
an aryloxyalkyl group optionally having substituent(s),
a heteroaryl group optionally having substituent(s) or
a heteroarylalkyl group optionally having substituent(s), or a pharmaceutically acceptable salt thereof, or a hydrate or solvate thereof;

[2] the carboxylic acid derivative of [1], which is represented by the following formula (I')

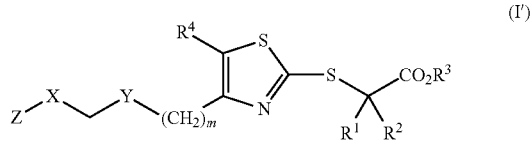

wherein R¹, R², R³, R⁴, m, X, Y and Z are as defined above, or a pharmaceutically acceptable salt thereof, or a hydrate or solvate thereof;

[3] the carboxylic acid derivative of [1] or [2], wherein R¹ and R² are the same or different and each is a $C_{1-15}$ alkyl group, R³ is a hydrogen atom or a $C_{1-15}$ alkyl group;

R⁴ is a hydrogen atom;

m is 0;

X is a bond or an oxygen atom;

Y is a carbonyl group or a group represented by —CH(OR⁵)— wherein R⁵ is a hydrogen atom or a $C_{1-15}$ alkyl group; and Z is a halogen atom, a $C_{1-15}$ alkyl group, a $C_{6-14}$ aryl group optionally having substituent(s) or a heteroaryl group optionally having substituent(s), or a pharmaceutically acceptable salt thereof, or a hydrate or solvate thereof;

[4] the carboxylic acid derivative of [1] or [2], wherein R¹ and R² are the same or different and each is a $C_{1-6}$ alkyl group, R³ is a hydrogen atom or a $C_{1-6}$ alkyl group;

R⁴ is a hydrogen atom;

m is 0;

X is a bond or an oxygen atom;

Y is a carbonyl group or a group represented by —CH(OR⁵)— wherein R⁵ is a hydrogen atom or a $C_{1-6}$ alkyl group; and Z is
(1) a halogen atom,
(2) a $C_{1-6}$ alkyl group,
(3) a $C_{6-14}$ aryl group optionally having 1 to 3 substituents selected from the group consisting of
  (i) $C_{1-6}$ alkyl,
  (ii) halo-$C_{1-6}$ alkyl,
  (iii) $C_{6-14}$ aryl and
  (iv) halo-$C_{6-14}$ aryl
or
(4) a heteroaryl group optionally having 1 to 3 substituents selected from the group consisting of
  (i) $C_{1-6}$ alkyl,
  (ii) halo-$C_{1-6}$ alkyl,
  (iii) $C_{6-14}$ aryl and
  (iv) halo-$C_{6-14}$ aryl,
or a pharmaceutically acceptable salt thereof, or a hydrate or solvate thereof;

[5] the carboxylic acid derivative of any one of [1] to [3], wherein, in the formula (I) or the formula (I'), an aryl group optionally having substituent(s) or a heteroaryl group optionally having substituent(s) for Z is represented by a substituent selected from the group consisting of the following formulas (Za-Zn)

(Za)

(Zb)

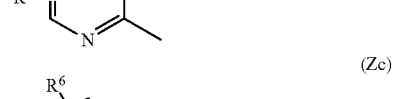

(Zc)

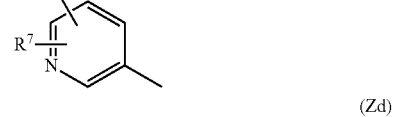

(Zd)

(Ze)

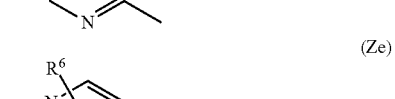

(Zf)

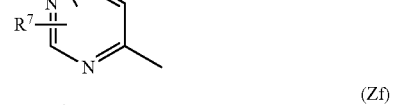

(Zg)

(Zh)

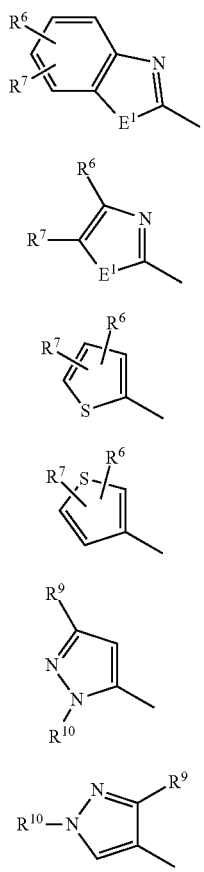

wherein
R⁶, R⁷, R⁸, R⁹ and R¹⁰ are the same or different and each is a hydrogen atom, a $C_{1-6}$ alkyl group, a halo-$C_{1-6}$ alkyl group, a $C_{6-14}$ aryl group or a halo-$C_{6-14}$ aryl group, and
$E^1$ is an oxygen atom, a sulfur atom or —$NR^{20}$— wherein $R^{20}$ is a hydrogen atom, a $C_{1-6}$ alkyl group, a $C_{3-7}$ cycloalkyl group, a $C_{6-14}$ aryl group, a $C_{6-14}$ aryl-$C_{1-6}$ alkyl group or a heteroaryl-$C_{1-6}$ alkyl group, or a pharmaceutically acceptable salt thereof, or a hydrate or solvate thereof;

[6] a carboxylic acid which is 2-[(4-{[(4'-fluorobiphenyl-4-yl)oxy]acetyl}-1,3-thiazol-2-yl)thio]-2-methylpropionic acid;
2-[(4-{2-[(4'-fluorobiphenyl-4-yl)oxy]-1-hydroxyethyl}-1,3-thiazol-2-yl)thio]-2-methylpropionic acid;
2-[(4-{[(4'-chlorobiphenyl-4-yl)oxy]acetyl}-1,3-thiazol-2-yl)thio]-2-methylpropionic acid;
2-[(4-{2-[(4'-chlorobiphenyl-4-yl)oxy]-1-hydroxyethyl}-1,3-thiazol-2-yl)thio]-2-methylpropionic acid;
2-[(4-{2-[(4'-fluorobiphenyl-4-yl)oxy]-1-methoxyethyl}-1,3-thiazol-2-yl)thio]-2-methylpropionic acid;
2-{[4-(2-{[5-(4-fluorophenyl)pyridin-2-yl]oxy}-1-hydroxyethyl)-1,3-thiazol-2-yl]thio}-2-methylpropionic acid;
2-[(4-{(1S)-2-[(4'-fluorobiphenyl-4-yl)oxy]-1-hydroxyethyl}-1,3-thiazol-2-yl)thio]-2-methylpropionic acid;
or
2-[(4-{(1R)-2-[(4'-fluorobiphenyl-4-yl)oxy]-1-hydroxyethyl}-1,3-thiazol-2-yl)thio]-2-methylpropionic acid;
or a derivative thereof or a pharmaceutically acceptable salt thereof, or a hydrate or solvate thereof;
[7] a prophylactic and/or therapeutic drug for a disease selected from hyperlipidemia, hyperlipidemia secondary to diabetes, arteriosclerosis, ischemic cardiac diseases and diabetes, which comprises the carboxylic acid derivative of any one of [1] to [6], or a pharmaceutically acceptable salt thereof, or a hydrate or solvate thereof, as an active ingredient;
[8] use of the carboxylic acid derivative of any one of [1] to [6] or a pharmaceutically acceptable salt thereof, or a hydrate or solvate thereof, for the manufacture of a medicament for the prophylaxis and/or treatment of a disease selected from hyperlipidemia, hyperlipidemia secondary to diabetes, arteriosclerosis, ischemic cardiac diseases and diabetes;
[9] a pharmaceutical composition comprising the carboxylic acid derivative of any one of [1] to [6] or a pharmaceutically acceptable salt thereof, or a hydrate or solvate thereof, and a pharmaceutically acceptable carrier;
[10] a method for the prophylaxis and/or treatment of a disease selected from hyperlipidemia, hyperlipidemia secondary to diabetes, arteriosclerosis, ischemic cardiac diseases and diabetes, comprising administering the carboxylic acid derivative of any one of [1] to [6] or a pharmaceutically acceptable salt thereof, or a hydrate or solvate thereof to a subject in need thereof; and
[11] the carboxylic acid derivative of any one of [1] to [6] or a pharmaceutically acceptable salt thereof, or a hydrate or solvate thereof, for the prophylaxis and/or treatment of diseases selected from hyperlipidemia, hyperlipidemia secondary to diabetes, arteriosclerosis, ischemic cardiac diseases and diabetes.

Effect of the Invention

The present invention can provide a compound having a PPARα agonist action, and useful as a drug for the prophylaxis and/or treatment of hyperlipidemia. In addition, the present invention can provide an intermediate useful for the synthesis of the above-mentioned compound.

DESCRIPTION OF EMBODIMENTS

The present invention is explained in detail in the following.
Specific examples of each group in the above-mentioned compound (I) are as follows.
The "alkyl group" of the "alkyl group optionally having substituent(s)" for $R^1$ or $R^2$ generally means a linear or branched chain alkyl group ($C_{1-15}$ alkyl group) having a carbon number of 1 to 15 and, for example, methyl, ethyl, propyl, isopropyl, butyl, isobutyl, sec-butyl, tert-butyl, pentyl, isopentyl, neopentyl, hexyl, heptyl, octyl, nonyl, decyl and the like can be mentioned. Preferably, a $C_{1-6}$ alkyl group such as methyl, ethyl, propyl, isopropyl, butyl, isobutyl, sec-butyl, tert-butyl, pentyl and the like can be mentioned. More preferred are methyl and ethyl, and the most preferred is methyl.
Examples of the substituent which the above-mentioned "alkyl group optionally having substituent(s)" may have include
(1) a halogen atom,
(2) $C_{1-15}$ alkyl (preferably, $C_{1-6}$ alkyl),
(3) halo-$C_{1-15}$ alkyl,
(4) $C_{6-14}$ aryl optionally having 1 to 3 substituents selected from the group consisting of
  (i) a halogen atom,
  (ii) hydroxy,
  (iii) nitro,
  (iv) cyano,
  (v) amino,
  (vi) $C_{1-15}$ alkyl,
  (vii) halo-$C_{1-15}$ alkyl, (viii) $C_{1-15}$ alkoxy and
(ix) halo-$C_{1-15}$ alkoxy,
(5) heteroaryl optionally having 1 to 3 substituents selected from the group consisting of
(i) a halogen atom,
(ii) hydroxy,
(iii) nitro,
(iv) cyano,
(v) amino,
(vi) $C_{1-15}$ alkyl,
(vii) halo-$C_{1-15}$ alkyl,
(viii) $C_{1-15}$ alkoxy and
(ix) halo-$C_{1-15}$ alkoxy,
(6) $C_{1-15}$ alkoxy,
(7) halo-$C_{1-15}$ alkoxy,
and the like.

Here, in the present specification, examples of the "halogen atom" include a fluorine atom, a chlorine atom, a bromine atom and an iodine atom.

In the present specification, examples of the "$C_{1-15}$ alkoxy" include methoxy and ethoxy. In addition, in the present specification, examples of the "halo-$C_{1-15}$ alkoxy" include the above-mentioned $C_{1-15}$ alkoxy substituted by one or more halogen atoms.

Examples of the "cycloalkyl group" of the "cycloalkyl group optionally having substituent(s)" for $R^1$ or $R^2$ include a cycloalkyl group having a carbon number of 3 to 7 ($C_{3-7}$ cycloalkyl group), and specific examples include cyclopropyl, cyclobutyl, cyclopentyl, cyclohexyl, cycloheptyl and the like. Preferably, cyclopropyl, cyclobutyl, cyclopentyl and cyclohexyl can be mentioned, and more preferably, cyclopropyl and cyclobutyl can be mentioned. Examples of the substituent which the "cycloalkyl group optionally having substituent(s)" may have include groups similar to the substituents which the "alkyl group optionally having substituent(s)" for $R^1$ or $R^2$ may have.

Examples of the "alkyl group" of the "alkyl group optionally having substituent(s)" for $R^3$ include groups similar to the "alkyl group" of the "alkyl group optionally having substituent(s)" for $R^1$ or $R^2$. Preferably, a $C_{1-6}$ alkyl group such as methyl, ethyl, propyl, isopropyl, butyl, isobutyl, sec-butyl, tert-butyl, pentyl and the like can be mentioned. More preferred are methyl, ethyl and tert-butyl, and the most preferred is tert-butyl. In addition, examples of the substituent which the group may have include groups similar to the substituents which the "alkyl group optionally having substituent(s)" for $R^1$ or $R^2$ may have.

Examples of the "alkyl group" of the "alkyl group optionally having substituent(s)" for $R^4$ include groups similar to the "alkyl group" of the "alkyl group optionally having substituent(s)" for $R^1$ or $R^2$. Preferred are a $C_{1-6}$ alkyl group such as methyl, ethyl, propyl, isopropyl, butyl, isobutyl, sec-butyl, tert-butyl and the like, and more preferred is methyl. In addition, examples of the substituent which the group may have include groups similar to the substituent which the "alkyl group optionally having substituent(s)" for $R^1$ or $R^2$ may have.

The "aryl group" of the "aryl group optionally having substituent(s)" for $R^4$ means an aryl group having a carbon number of 6 to 14 ($C_{6-14}$ aryl group) and, for example, a phenyl, naphthyl or ortho-fused bicyclic group having 8 to 10 ring atoms wherein at least one ring is an aromatic ring (e.g., indenyl etc.) and the like can be mentioned. Examples of the substituent which the group may have include groups similar to the substituent which the "alkyl group optionally having substituent(s)" for $R^1$ or $R^2$ may have.

Examples of the "alkyl group" of the "alkyl group optionally having substituent(s)" for $R^5$ include groups similar to the "alkyl group" of the "alkyl group optionally having substituent(s)" for $R^1$ or $R^2$. Preferred is an alkyl group having a carbon number of 1 to 6 ($C_{1-6}$ alkyl group), and more preferred is methyl. In addition, examples of the substituent which the group may have include groups similar to the substituent which the "alkyl group optionally having substituent(s)" for $R^1$ or $R^2$ may have.

Examples of the "halogen atom" for Z include a fluorine atom, a bromine atom, a chlorine atom and an iodine atom. Preferred are a bromine atom and a chlorine atom.

Examples of the "alkyl group" of the "alkyl group optionally having substituent(s)" for Z include groups similar to the "alkyl group" of the "alkyl group optionally having substituent(s)" for $R^1$ or $R^2$. Preferred is an alkyl group having a carbon number of 1 to 6 ($C_{1-6}$ alkyl group), and more preferred is methyl. In addition, examples of the substituent which the group may have include groups similar to the substituent which the "alkyl group optionally having substituent(s)" for $R^1$ or $R^2$ may have.

Examples of the "cycloalkyl group" of the "cycloalkyl group optionally having substituent(s)" for Z include groups similar to the "cycloalkyl group" of the "cycloalkyl group optionally having substituent(s)" for $R^1$ or $R^2$. Preferred is cyclohexyl. In addition, examples of the substituent which the group may have include groups similar to the substituent which the "alkyl group optionally having substituent(s)" for $R^1$ or $R^2$ may have.

The "aryl group" of the "aryl group optionally having substituent(s)" for Z means an aryl group having a carbon number of 6 to 14 ($C_{6-14}$ aryl group) and, for example, a phenyl, naphthyl or ortho-fused bicyclic group having 8 to 10 ring atoms and at least one aromatic ring (e.g., indenyl etc.) and the like can be mentioned. Preferred are phenyl and naphthyl, and more preferred is phenyl.

Examples of the substituent which the aryl group may have include, in addition to the substituents (1)-(7) which the "alkyl group optionally having substituent(s)" for $R^1$ or $R^2$ may have, substituents selected from
(8) a cyano group,
(9) a nitro group,
(10) —$NR^{11}R^{12}$,
(11) —$NR^{13}COR^{14}$,
(12) —$CONR^{15}R^{16}$
(13) —$OR^{17}$,
(14) —$COR^{18}$ and
(15) —$C \equiv CR^{19}$
wherein
$R^{11}$, $R^{12}$, $R^{13}$, $R^{14}$, $R^{15}$ and $R^{16}$ are the same or different and each is a hydrogen atom, a $C_{1-15}$ alkyl group, a $C_{3-7}$ cycloalkyl group, a $C_{6-14}$ aryl group, a $C_{6-14}$ aryl-$C_{1-6}$ alkyl group, a heteroaryl group or a heteroaryl-$C_{1-6}$ alkyl group, or $R^{11}$ and $R^{12}$, and $R^{13}$ and $R^{14}$ are bonded to each other to form a hetero ring optionally having a carbon and a hetero atom; and $R^{17}$, $R^{18}$ and $R^{19}$ are each independently a hydrogen atom, a $C_{1-15}$ alkyl group, a $C_{3-7}$ cycloalkyl group, a $C_{6-14}$ aryl group, a $C_{6-14}$ aryl-$C_{1-6}$ alkyl group, a heteroaryl group or a heteroaryl-$C_{1-6}$ alkyl group. Preferred is $C_{6-14}$ aryl optionally having 1 to 3 substituents selected from the group consisting of
(i) a halogen atom,
(ii) hydroxy,
(iii) nitro,
(iv) cyano,
(v) amino, (vi) $C_{1-15}$ alkyl,
(vii) halo-$C_{1-15}$ alkyl,
(viii) $C_{1-15}$ alkoxy and
(ix) halo-$C_{1-15}$ alkoxy,
and more preferred is $C_{6-14}$ aryl optionally substituted by halo-$C_{6-14}$ aryl.

In the "arylalkyl group" of the "arylalkyl group optionally having substituent(s)" for Z, the aryl moiety is equivalent to the "aryl group" of the "aryl group optionally having substituent(s)" for Z, and the alkyl moiety is a linear or branched chain alkyl group having a carbon number 1 to 8. Examples thereof include $C_{6-14}$ aryl-$C_{1-8}$ alkyl such as benzyl, benzhydryl, 1-phenylethyl, 2-phenylethyl, phenylpropyl, phenylbutyl, phenylpentyl, phenylhexyl, naphthylmethyl, naphthylethyl and the like. Preferred are benzyl and naphthylmethyl. In addition, examples of the substituent which the group may have include groups similar to the substituent which the "aryl group optionally having substituent(s)" for Z may have.

The "arylalkenyl group" of the "arylalkenyl group optionally having substituent(s)" for Z means a group wherein the "aryl group" of the "aryl group optionally having substituent(s)" for Z is bonded to an alkenyl group having a carbon number of 2 to 6. Specific examples thereof include $C_{6-14}$ aryl-$C_{2-6}$ alkenyl such as 1-phenylethenyl, 2-phenylethenyl, 1-phenyl-1-propenyl, 2-phenyl-1-propenyl, 3-phenyl-1-propenyl, 1-phenyl-2-propenyl, 2-phenyl-2-propenyl, 3-phenyl-2-propenyl, 1-phenyl-1-butenyl, 2-phenyl-1-butenyl, 3-phenyl-2-butenyl, 4-phenyl-2-butenyl, 3-phenyl-2-propenyl, 2-phenyl-1-pentenyl, 2-phenyl-3-pentenyl, 2-phenyl-1-hexenyl and the like. In addition, examples of the substituent which the group may have include groups similar to the substituent which the "aryl group optionally having substituent(s)" for Z may have.

The "aryloxyalkyl group" of the "aryloxyalkyl group optionally having substituent(s)" for Z means a group wherein the "aryl group" of the "aryl group optionally having substituent(s)" for Z is bonded to a linear or branched alkyl group having a carbon number of 1 to 8 via an oxygen atom. Specific examples thereof include $C_{6-14}$ aryloxy-$C_{1-8}$ alkyl such as a (phenyloxy)methyl group, a (1-naphthyloxy)methyl group, a (2-naphthyloxy)methyl group, a 1-(phenyloxy)ethyl group, a 2-(phenyloxy)ethyl group, a 1-(1-naphthyloxy)ethyl group, a 2-(1-naphthyloxy)ethyl group, a 1-(phenyloxy)propyl group, a 2-(phenyloxy)propyl group, a 3-(phenyloxy) propyl group, a 4-(phenyloxy)butyl group, a 5-(phenyloxy) pentyl group, a 6-(phenyloxy)hexyl group and the like. In addition, examples of the substituent which the group may have include groups similar to the substituent which the "aryl group optionally having substituent(s)" for Z may have.

Examples of the "heteroaryl group" of the "heteroaryl group optionally having substituent(s)" for Z include a 5- or 6-membered ring group having carbon and 1 to 4 hetero atoms (oxygen, sulfur or nitrogen), or ortho-fused bicyclic heteroaryl having 8 to 10 ring atoms, which is induced therefrom, particularly a benz derivative, or one derived by fusing propenylene, trimethylene or tetramethylene group therewith, a stable N-oxide thereof and the like. Specific examples thereof include pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,4-oxadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, benzoxazolyl, benzisoxazolyl, benzothiazolyl, benzisothiazolyl, benzimidazolyl, oxazolopyridyl, imidazopyridazinyl, thianaphthenyl, isothianaphthenyl, benzofuranyl, isobenzofuranyl, benzothienyl, chromenyl, isoindolyl, indolyl, indolinyl, indazolyl, isoquinolyl, quinolyl, phthalazinyl, quinoxalinyl, quinazolinyl, cinnolinyl, 2,1,3-benzoxadiazolyl, benzoxazinyl and the like. In addition, examples of the substituent which the group may have include groups similar to the substituent which the "aryl group optionally having substituent(s)" for Z may have.

The "heteroarylalkyl group" of the "heteroarylalkyl group optionally having substituent(s)" for Z is a group wherein the heteroaryl moiety is a group similar to the "heteroaryl group" of the "heteroaryl group optionally having substituent(s)" for Z, and the alkyl moiety is a linear or branched alkyl group having a carbon number of 1 to 3. Examples of such group include a heteroaryl-$C_{1-3}$ alkyl group such as 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyridyl)ethyl, 3-(2-pyrrolyl)propyl, 4-imidazolylmethyl and the like.

Preferable example of $R^1$ is a $C_{1-15}$ alkyl group. More preferred is a $C_{1-6}$ alkyl group, and the most preferred is a methyl group.

Preferable example of $R^2$ is a $C_{1-15}$ alkyl group. More preferred is a $C_{1-6}$ alkyl group, and the most preferred is a methyl group.

Preferable example of $R^3$ is a hydrogen atom or a $C_{1-15}$ alkyl group. More preferred is a hydrogen atom or a $C_{1-6}$ alkyl group, and the most preferred is a hydrogen atom or a tert-butyl group.

Preferable example of $R^4$ is a hydrogen atom, a $C_{1-15}$ alkyl group or a $C_{6-14}$ aryl group. More preferred is a hydrogen atom.

Preferable example of m is an integer of 0 to 3. More preferred is 0 or 1, and the most preferred is 0.

Preferable example of X is a bond, an oxygen atom or a sulfur atom. More preferred is a bond or an oxygen atom.

Preferable example of Y is a carbonyl group or a group represented by —CH(OR$^5$)— (preferable example of $R^5$ is a hydrogen atom or $C_{1-15}$ alkyl. More preferred is a hydrogen atom or $C_{1-6}$ alkyl, and the most preferred is a hydrogen atom or methyl).

Preferable example of Z is
(1) a halogen atom,
(2) a $C_{1-15}$ alkyl group optionally having substituent(s),
(3) a $C_{3-7}$ cycloalkyl group optionally having substituent(s),
(4) a $C_{6-14}$ aryl group optionally having substituent(s),
(5) a $C_{6-14}$ aryl-$C_{1-8}$ alkyl group optionally having substituent(s),
(6) a $C_{6-14}$ aryl-$C_{2-6}$ alkenyl group optionally having substituent(s),
(7) a $C_{6-14}$ aryloxy-$C_{1-8}$ alkyl group optionally having substituent(s),
(8) a heteroaryl group optionally having substituent(s) or
(9) a heteroaryl-$C_{1-3}$ alkyl group optionally having substituent(s), more preferably,
(1) a halogen atom,
(2) a $C_{1-15}$ alkyl group,
(3) a $C_{6-14}$ aryl group optionally having substituent(s) or
(4) a heteroaryl group optionally having substituent(s), further preferably,
(1) a halogen atom,
(2) a $C_{1-6}$ alkyl group,
(3) a $C_{6-14}$ aryl group optionally having 1 to 3 substituents selected from the group consisting of
   (i) $C_{1-6}$ alkyl,
   (ii) halo-$C_{1-6}$ alkyl,
   (iii) $C_{6-14}$ aryl and
   (iv) halo-$C_{6-14}$ aryl, and (4) a heteroaryl group optionally having 1 to 3 substituents selected from the group consisting of
  (i) $C_{1-6}$ alkyl,
  (ii) halo-$C_{1-6}$ alkyl,
  (iii) $C_{6-14}$ aryl and
  (iv) halo-$C_{6-14}$ aryl.

The most preferred is a chlorine atom, a bromine atom, a methyl group, a fluorobiphenyl group, a chlorobiphenyl group or a fluorophenyl-pyridinyl group.

When Z is an aryl group optionally having substituent(s) or a heteroaryl group optionally having substituent(s), these groups are preferably selected from the following formulas (Za-Zn)

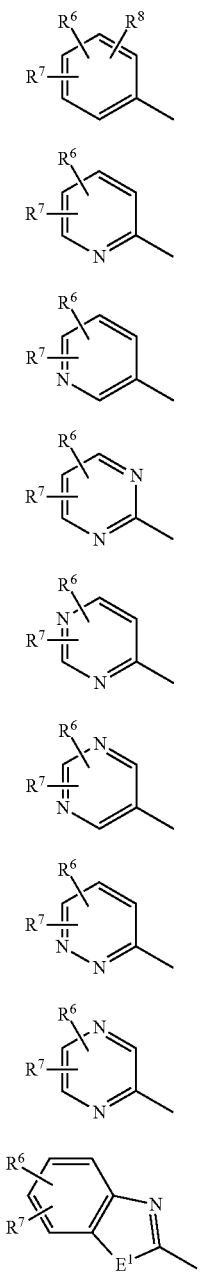

(Za)
(Zb)
(Zc)
(Zd)
(Ze)
(Zf)
(Zg)
(Zh)
(Zi)

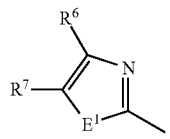

(Zj)

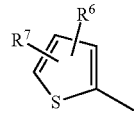

(Zk)

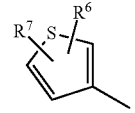

(Zl)

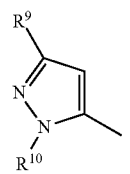

(Zm)

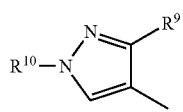

(Zn)

wherein
$R^6$, $R^7$ and $R^8$ are the same or different and each is
(1) a hydrogen atom,
(2) a halogen atom,
(3) a $C_{1-6}$ alkyl group,
(4) a halo-$C_{1-6}$ alkyl group,
(5) a $C_{6-14}$ aryl group optionally having 1 to 3 substituents selected from the group consisting of
  (i) a halogen atom,
  (ii) hydroxy,
  (iii) nitro,
  (iv) cyano,
  (v) amino,
  (vi) $C_{1-15}$ alkyl,
  (vii) halo-$C_{1-15}$ alkyl,
  (viii) $C_{1-15}$ alkoxy and
  (ix) halo-$C_{1-15}$ alkoxy,
(6) a heteroaryl group optionally having 1 to 3 substituents selected from the group consisting of
  (i) halogen atom,
  (ii) hydroxy,
  (iii) nitro,
  (iv) cyano,
  (v) amino,
  (vi) $C_{1-15}$ alkyl,
  (vii) halo-$C_{1-15}$ alkyl,
  (viii) $C_{1-15}$ alkoxy and
  (ix) halo-$C_{1-15}$ alkoxy,
(7) a $C_{1-6}$ alkoxy group,
(8) a halo-$C_{1-6}$ alkoxy group,
(9) a cyano group,
(10) a nitro group,
(11) —$NR^{11}R^{12}$,
(12) —$NR^{13}COR^{14}$,
(13) —$CONR^{15}R^{16}$ wherein
$R^{11}$, $R^{12}$, $R^{13}$, $R^{14}$, $R^{15}$ and $R^{16}$ are the same or different and each is a hydrogen atom, a $C_{1-6}$ alkyl group, a $C_{3-7}$ cycloalkyl group, a $C_{6-14}$ aryl group, a $C_{6-14}$ aryl-$C_{1-6}$ alkyl group, a heteroaryl group or a heteroaryl-$C_{1-6}$ alkyl group, or
$R^{11}$ and $R^{12}$, and $R^{13}$ and $R^{14}$ are bonded to each other to form a hetero ring),

(14) —$OR^{17}$,
(15) —$COR^{18}$ or
(16) —C≡$CR^{19}$ wherein $R^{17}$, $R^{18}$ and $R^{19}$ are each independently a hydrogen atom, a $C_{1-6}$ alkyl group, a $C_{3-7}$ cycloalkyl group, a $C_{6-14}$ aryl group, a $C_{6-14}$ aryl-$C_{1-6}$ alkyl group, a heteroaryl group or a heteroaryl-$C_{1-6}$ alkyl group;

$R^9$ is a hydrogen atom, a halogen atom, a $C_{1-6}$ alkyl group, a $C_{3-7}$ cycloalkyl group, a halo-$C_{1-6}$ alkyl group, a $C_{6-14}$ aryl group, a halo-$C_{6-14}$ aryl group, a heteroaryl group, a cyano group or a nitro group;

$R^{10}$ is a hydrogen atom, a $C_{1-6}$ alkyl group, a $C_{3-7}$ cycloalkyl group, a halo-$C_{1-6}$ alkyl group, a $C_{6-14}$ aryl group, a halo-$C_{6-14}$ aryl group, a $C_{6-14}$ aryl-$C_{1-6}$ alkyl group, a heteroaryl group or a heteroaryl-$C_{1-6}$ alkyl group; and $E^1$ is an oxygen atom, a sulfur atom or —$NR^{20}$— wherein $R^{20}$ is a hydrogen atom, a $C_{1-6}$ alkyl group, a $C_{3-7}$ cycloalkyl group, a $C_{6-14}$ aryl group, a $C_{6-14}$ aryl-$C_{1-6}$ alkyl group or a heteroaryl-$C_{1-6}$ alkyl group.

Examples of the $C_{1-6}$ alkyl group for $R^6$, $R^7$ or $R^8$ include groups similar to the $C_{1-6}$ alkyl group for $R^1$ or $R^2$.

Examples of the halogen atom for $R^6$, $R^7$ or $R^8$ include a fluorine atom, a bromine atom, a chlorine atom and an iodine atom.

Examples of the halo-$C_{1-6}$ alkyl group for $R^6$, $R^7$ or $R^8$ include a $C_{1-6}$ alkyl group substituted by a halogen atom, such as fluoromethyl, difluoromethyl, trifluoromethyl, chloromethyl, 2,2,2-trifluoroethyl, pentafluoroethyl and the like.

Examples of the $C_{6-14}$ aryl group for $R^6$, $R^7$ or $R^8$ include groups similar to the "aryl group" of the "aryl group optionally having substituent(s)" for $R^4$, with preference given to a phenyl group.

Examples of the heteroaryl group for $R^6$, $R^7$ or $R^8$ include groups similar to the "heteroaryl group" of the "heteroaryl group optionally having substituent(s)" for Z, with preference given to pyridyl and pyrimidyl.

Examples of the alkoxy group for $R^6$, $R^7$ or $R^8$ include a $C_{1-15}$ alkoxy group, which is specifically methoxy or ethoxy.

Examples of the haloalkoxy group for $R^6$, $R^7$ or $R^8$ include the aforementioned alkoxy group which is substituted by a halogen atom, such as trifluoromethoxy, 2,2,2-trifluoroethoxy, difluoromethoxy and the like.

Preferable examples of the halogen atom for $R^9$ include a chlorine atom and a bromine atom.

Examples of the $C_{1-6}$ alkyl group for $R^9$ or $R^{10}$ include groups similar to the $C_{1-6}$ alkyl group for $R^1$ or $R^2$.

Examples of the $C_{3-7}$ cycloalkyl group for $R^9$ or $R^{10}$ include groups similar to the $C_{3-7}$ cycloalkyl group for $R^1$ or $R^2$, with preference given to cyclohexyl.

Examples of the halo-$C_{1-6}$ alkyl group for $R^9$ or $R^{10}$ include fluoromethyl, difluoromethyl, trifluoromethyl, chloromethyl, 2,2,2-trifluoroethyl, pentafluoroethyl and the like.

Examples of the $C_{6-14}$ aryl group for $R^9$ or $R^{10}$ include groups similar to the aryl group for $R^4$, with preference given to a phenyl group.

Preferable examples of the halo-$C_{6-14}$ aryl group for $R^9$ or $R^{10}$ include chlorophenyl and bromophenyl.

Examples of the heteroaryl group for $R^9$ or $R^{10}$ include groups similar to the heteroaryl group for Z, with preference given to pyridyl and pyrimidyl.

Examples of the $C_{6-14}$ aryl-$C_{1-6}$ alkyl group for $R^{10}$ include groups similar to the $C_{6-14}$ aryl-$C_{1-8}$ alkyl group for Z.

Examples of the heteroaryl-$C_{1-6}$ alkyl group for $R^{10}$ include groups similar to the heteroaryl-$C_{1-3}$ alkyl group for Z.

Examples of the $C_{1-6}$ alkyl group for $R^{11}$, $R^{12}$, $R^{13}$, $R^{14}$, $R^{15}$ or $R^{16}$ include groups similar to the $C_{1-6}$ alkyl group for $R^1$ or $R^2$.

Examples of the $C_{3-7}$ cycloalkyl group for $R^{11}$, $R^{12}$, $R^{13}$, $R^{14}$, $R^{15}$ or $R^{16}$ include groups similar to the $C_{3-7}$ cycloalkyl group for $R^1$ or $R^2$, with preference given to cyclohexyl.

Examples of the $C_{6-14}$ aryl group for $R^{11}$, $R^{12}$, $R^{13}$, $R^{14}$, $R^{15}$ or $R^{16}$ include groups similar to the aryl group for $R^4$, with preference given to a phenyl group.

Examples of the $C_{6-14}$ aryl-$C_{1-6}$ alkyl group for $R^{11}$, $R^{12}$, $R^{13}$, $R^{14}$, $R^{15}$ or $R^{16}$ include groups similar to the $C_{6-14}$ aryl-$C_{1-6}$ alkyl group for Z.

Examples of the heteroaryl group for $R^{11}$, $R^{12}$, $R^{13}$, $R^{14}$, $R^{15}$ or $R^{16}$ include groups similar to the heteroaryl group for Z, with preference given to pyridyl and pyrimidyl.

Examples of the heteroaryl-$C_{1-6}$ alkyl group for $R^{11}$, $R^{12}$, $R^{13}$, $R^{14}$, $R^{15}$ or $R^{16}$ include groups similar to the heteroarylalkyl group for Z.

Examples of the hetero ring for $R^{11}$ or $R^{12}$, and $R^{13}$ or $R^{14}$ include a nonaromatic heterocyclic group having 2 to 10 carbon atoms, which contains, as a ring-constituting atom besides carbon atom, 1 to 3 hetero atoms selected from oxygen atom, sulfur atom and nitrogen atom. For example, azetidinyl, pyrrolidinyl, piperidino, piperazino, morpholino, 1,2,5,6-tetrahydropyridyl, thiomorpholino, oxothiomorpholino, dioxothiomorpholino, 3-azaspiro[5,5]undecyl, 1,3,8-triazaspiro[4,5]decyl and the like can be mentioned.

Examples of the $C_{1-6}$ alkyl group for $R^{17}$, $R^{18}$, $R^{19}$ or $R^{20}$ include groups similar to the $C_{1-6}$ alkyl group for $R^1$ or $R^2$.

Examples of the $C_{3-7}$ cycloalkyl group for $R^{17}$, $R^{18}$, $R^{19}$ or $R^{20}$ include groups similar to the $C_{3-7}$ cycloalkyl group for $R^1$, with preference given to cyclohexyl.

Examples of the $C_{6-14}$ aryl group for $R^{17}$, $R^{18}$, $R^{19}$ or $R^{20}$ include groups similar to the $C_{6-14}$ aryl group for $R^4$, with preference given to a phenyl group.

Examples of the $C_{6-14}$ aryl-$C_{1-8}$ alkyl group for $R^{17}$, $R^{18}$, $R^{19}$ or $R^{20}$ include groups similar to the $C_{6-14}$ aryl-$C_{1-8}$ alkyl group for Z.

Examples of the heteroaryl group for $R^{17}$, $R^{18}$ or $R^{19}$ include groups similar to the heteroaryl group for Z, with preference given to pyridyl and pyrimidyl.

Examples of the heteroaryl-$C_{1-6}$ alkyl group for $R^{17}$, $R^{18}$, $R^{19}$ or $R^{20}$ include groups similar to the heteroaryl-$C_{1-3}$ alkyl group for Z.

Particularly preferred as $R^6$, $R^7$, $R^8$, $R^9$ or $R^{10}$ is a hydrogen atom, a $C_{1-6}$ alkyl group, a halo-$C_{1-6}$ alkyl group, a $C_{6-14}$ aryl group or a halo-$C_{6-14}$ aryl group.

Preferable examples of compound (I) include a carboxylic acid derivative represented by the formula (I)
wherein
$R^1$ and $R^2$ are the same or different and each is a $C_{1-15}$ alkyl group,
$R^3$ is a hydrogen atom or a $C_{1-15}$ alkyl group;
$R^4$ is a hydrogen atom;
m is 0;
X is a bond or an oxygen atom;
Y is a carbonyl group or a group represented by —CH($OR^5$)— wherein $R^5$ is a hydrogen atom or a $C_{1-15}$ alkyl group; and Z is a halogen atom, a $C_{1-15}$ alkyl group, a $C_{6-14}$ aryl group optionally having substituent(s) or a heteroaryl group optionally having substituent(s).

More preferable examples of compound (I) include a carboxylic acid derivative represented by the formula (I), wherein $R^1$ and $R^2$ are the same or different and each is a $C_{1-6}$ alkyl group, $R^3$ is a hydrogen atom or a $C_{1-6}$ alkyl group;

$R^4$ is a hydrogen atom;

m is 0;

X is a bond or an oxygen atom;

Y is a carbonyl group or a group represented by —CH($OR^5$)— wherein $R^5$ is a hydrogen atom or a $C_{1-6}$ alkyl group; and Z is (1) a halogen atom, (2) a $C_{1-6}$ alkyl group, (3) a $C_{6-14}$ aryl group optionally having 1 to 3 substituents selected from the group consisting of
  (i) $C_{1-6}$ alkyl,
  (ii) halo-$C_{1-6}$ alkyl,
  (iii) $C_{6-14}$ aryl and
  (iv) halo-$C_{6-14}$ aryl, or (4) a heteroaryl group optionally having 1 to 3 substituents selected from the group consisting of
  (i) $C_{1-6}$ alkyl,
  (ii) halo-$C_{1-6}$ alkyl,
  (iii) $C_{6-14}$ aryl and
  (iv) halo-$C_{6-14}$ aryl.

In addition, a preferable embodiment of the present invention is a carboxylic acid derivative containing a thiazole ring, which is represented by the formula (II)

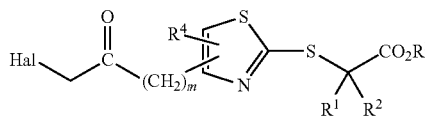

(II)

wherein $R^1$, $R^2$, $R^3$, $R^4$ and m are groups similar to those mentioned above, and Hal is a halogen atom similar to the one mentioned above (hereinafter to be described as compound (II)) or a pharmaceutically acceptable salt thereof, or a hydrate or solvate thereof.

Furthermore, a preferable embodiment of the present invention is a carboxylic acid derivative containing a thiazole ring, which is represented by the formula (IV)

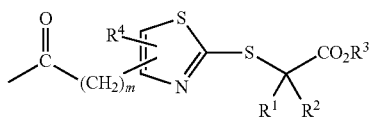

(IV)

wherein $R^1$, $R^2$, $R^3$, $R^4$ and m are groups similar to those mentioned above (hereinafter to be described as compound (IV)) or a pharmaceutically acceptable salt thereof, or a hydrate or solvate thereof.

Pharmaceutically acceptable salt of compound (I) includes any salt, and examples of thereof include salts with inorganic acid such as hydrochloric acid, hydrobromic acid and the like, salts with organic acid, salts with alkali metal, salts with organic base and salts with amino acid.

In the present invention, compound (I) or a pharmaceutically acceptable salt thereof encompasses any solvate (e.g., hydrate), prodrug to be converted to compound (I) or a pharmaceutically acceptable salt thereof by being metabolized in the body, and an active metabolite of the aforementioned compound (I).

Compound (I) of the present invention can be synthesized, for example, by the following methods; however, the production method thereof is not limited thereto.

Of compounds (I), a compound represented by the formula (I-1) wherein the Y moiety is a carbonyl group (hereinafter to be described as compound (I-1)), and a compound represented by (I-2) (hereinafter to be described as compound (I-2)) can be produced, for example, by the following method (production method 1).

[Production Method 1]

A compound represented by the formula (II-1) having a leaving group on the alkyl chain (hereinafter to be described as compound (II-1) etc., synthesis method is mentioned below) is reacted with an alcohol (thiol) derivative represented by the formula (III-1) (hereinafter to be described as compound (III-1) etc.) in the presence of a base to give compound (I-1) which is an ether (thioether) compound (step 1). Furthermore, the present compound can be converted to compound (I-2), which is a carboxylic acid compound, by de-esterification (step 2). Compound (III-1), which is a starting compound, is generally synthesized easily by a known method.

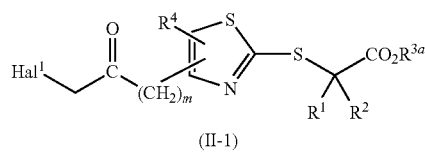

(II-1)

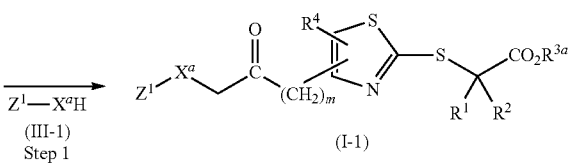

(III-1)
Step 1

(I-1)

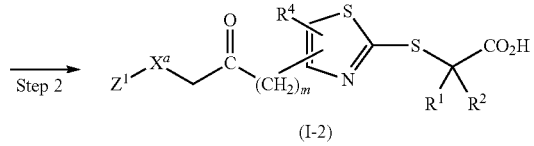

Step 2

(I-2)

wherein $R^1$, $R^2$, $R^4$ and m are as defined above, $R^{3a}$ is an alkyl group, $X^a$ is an oxygen atom or a sulfur atom, $Z^1$ is an optionally substituted aryl group or an optionally substituted heteroaryl group, and $Hal^1$ is a halogen atom.

Here, examples of the "alkyl group" for $R^{3a}$ include groups similar to the "alkyl group" of the "alkyl group optionally having substituent(s)" for $R^3$.

Examples of the "optionally substituted aryl group" for $Z^1$ include groups similar to the "aryl group" of the "aryl group optionally having substituent(s)" for Z.

Examples of the "optionally substituted heteroaryl group" for $Z^1$ include groups similar to the "heteroaryl group" of the "heteroaryl group optionally having substituent(s)" for Z.

Step 1 is generally performed in the presence of a base, in a solvent that does not adversely influence the reaction. As the base, for example, alkali metal carbonates such as potassium carbonate, sodium carbonate, cesium carbonate and the like, alkali metal alkoxides such as sodium methoxide, sodium ethoxide, potassium tertiary butoxide and the like, alkali metal hydroxides such as potassium hydroxide, sodium hydroxide, lithium hydroxide and the like, metal hydrides such as potassium hydride, sodium hydride and the like, amines such as triethylamine, N,N-diisopropylethylamine, N-methylmorpholine, pyridine, N,N-dimethylaniline, 4-dimethylaminopyridine, 1,8-diazabicyclo[5.4.0]undec-7-en and the like, and the like are used. The amount of the base to be used is preferably 1-5 molar equivalents, relative to compound (II-1). The reaction can be performed generally at −50 to 200° C., preferably −10 to 100° C. As the solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, amides such as N,N-dimethylformamide, N-methyl-2-pyrrolidone and the like, sulfoxides such as dimethyl sulfoxide and the like, alcohols such as methanol, ethanol and the like, ketones such as acetone and the like, nitriles such as acetonitrile, propionitrile and the like, water and the like are used. These solvents may be mixed at an appropriate ratio and used as a mixture. When a mixed solvent of water and the above-mentioned solvent is used as a solvent, a phase-transfer catalyst such as tetrabutylammonium iodide and the like may be used. The amount of compound (III-1) to be used is generally 0.5-5 equivalents, preferably 0.9-1.1 equivalents, relative to compound (II-1).

Step 2 is generally performed in the presence of an acid or base, in an aqueous solvent. As the acid, for example, formic acid, hydrochloric acid, sulfuric acid, acetic acid, hydrobromic acid, trifluoroacetic acid and the like are used. As the base, for example, alkali metal carbonates such as potassium carbonate, sodium carbonate and the like, alkali metal alkoxides such as sodium methoxide, sodium ethoxide and the like, alkali metal hydroxides such as potassium hydroxide, sodium hydroxide, lithium hydroxide and the like, and the like are used. The acid or base is generally used in an excess amount relative to compound (I-1). Preferably, the amount of the acid to be used is 2-100 molar equivalents relative to compound (I-1), and the amount of the base to be used is 1.2-5 molar equivalents relative to compound (I-1). As the aqueous solvent, for example, a mixed solvent of one or more kinds of solvents selected from alcohols such as methanol, ethanol and the like, ethers such as tetrahydrofuran, dioxane and the like, dimethyl sulfoxide, acetone and the like and water, and the like are used. When $R^3$ is a tert-butyl group, acid decomposition can be performed in addition to the above-mentioned reaction in an aqueous solvent. As the acid to be used for the acid decomposition, for example, formic acid, hydrochloric acid, sulfuric acid, acetic acid, hydrobromic acid, trifluoroacetic acid, methanesulfonic acid, para-toluenesulfonic acid and the like are used. In this case, the solvents may be mixed at an appropriate ratio. As such solvent, halogenated hydrocarbons such as chloroform, dichloromethane, dichloroethane etc. and the like are used. The amount of the acid to be used is generally an excess amount relative to compound (I-1). Preferably, the amount of the acid to be used is 2-100 molar equivalents relative to compound (I-1). The reaction temperature is generally −20 to 150° C., preferably −10 to 100° C.

In addition, a compound of the formula (I-1) can also be produced, for example, by the following method (production method 2).

[Production Method 2]

An ether (thioether) compound represented by the formula (I-1) can also be obtained by reacting a compound represented by the formula (II-1) having a leaving group on the alkyl chain (synthesis method is mentioned below) with a metal alkoxide derivative represented by the formula (III-2) in the presence of a base (step 3). Generally, compound (III-2) (starting compound) is synthesized easily according to a known method.

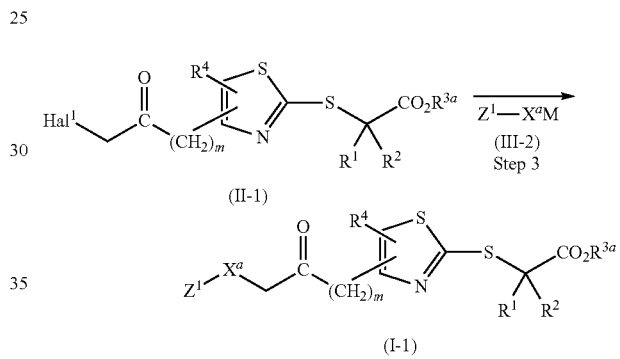

wherein $R^1$, $R^2$, $R^{3a}$, $R^4$, m, $Hal^1$, $X^a$ and $Z^1$ are as defined above, and M is a metal such as sodium, potassium, calcium, cesium, silver and the like.

Step 3 can be generally performed at −50 to 200° C., preferably −10 to 100° C., in a solvent that does not adversely influence the reaction. Examples of the solvent that does not adversely influence the reaction include alcohols such as methanol, ethanol and the like, ketones such as acetone and the like, nitriles such as acetonitrile, propionitrile and the like, hydrocarbons such as benzene, toluene and the like, water and the like are used. These solvents may be mixed at an appropriate ratio and used in a mixture. The amount of compound (III-2) to be used is generally 0.5-5 equivalents, preferably 1-2 equivalents, relative to compound (II-1).

Of the compounds represented by the formula (I), a compound represented by the formula (I-3) wherein Y moiety is —CH(OH)— (hereinafter to be described as compound (I-3) etc.) and a compound represented by the formula (I-4) (hereinafter to be described as compound (I-4)) can be produced, for example, according to the following method (production method 3).

[Production Method 3]

The alcohol compound (compound (I-3)) is obtained by reducing compound (I-1) obtained in production method 1 or 2 (step 4). Furthermore, the present compound can be converted to a carboxylic acid compound (compound (I-4)) by de-esterification (step 5).

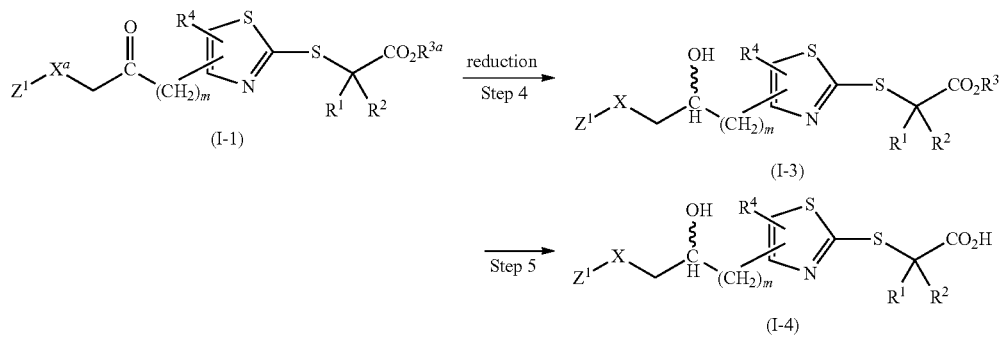

(I-1)

(I-3)

(I-4)

wherein $R^1$, $R^2$, $R^{3a}$, $R^4$, m, X and $Z^1$ are as defined above.

Step 4 is performed in a solvent that does not adversely influence the reaction in the presence of a reducing agent. As the reducing agent, metal borohydride compounds such as sodium borohydride, lithium borohydride and the like are used. The amount of the reducing agent to be used is preferably 1-5 molar equivalents relative to compound (I-1). The reaction temperature is generally −50 to 150° C., preferably −10 to 50° C. As the solvent that does not adversely influence the reaction, alcohols such as methanol, ethanol and the like are used. These solvents may be mixed at an appropriate ratio and used in a mixture. Step 5 can be performed in the same manner as in step 2, except that compound (I-1) in step 2 is changed to compound (I-3).

Of the compounds of the formula (I), a compound represented by the formula (I-6) (hereinafter to be described as compound (I-6)), a compound represented by the formula (I-7) (hereinafter to be described as compound (I-7)), a compound represented by the formula (I-8) (hereinafter to be described as compound (I-8)), and a compound represented by the formula (I-9) (hereinafter to be described as compound (I-9)), wherein Z is an aryl group or a heteroaryl group, and an aryl group or a heteroaryl group is present on the ring of the aryl group or heteroaryl group, can also be produced by, for example, the following method (production method 4), in addition to the methods shown in production methods 1 to 3.

[Production Method 4]

A compound represented by the formula (I-5) (hereinafter to be described as compound (I-5)), which is a compound represented by the formula (I) wherein Z is an aryl group or a heteroaryl group, and a leaving group such as a halogen atom, a trifluoromethanesulfonyloxy group and the like is present on the ring of the aryl group or heteroaryl group, is reacted with a boron compound represented by the formula (III-3) (hereinafter to be described as compound (III-3)) or a tin compound represented by the formula (III-4) (hereinafter to be described as compound (III-4)) in the presence of a metal catalyst to give compound (I-6) into which an aryl group or heteroaryl group is introduced (step 6). Moreover, this compound can be converted to compound (I-7), which is a carboxylic acid compound, by deesterification (step 7). In the same manner as in production method 3, it can be converted to compound (I-8) (alcohol compound) (step 8), and converted to compound (I-9) (carboxylic acid compound) by deesterification (step 9). Generally, compound (III-3) and compound (III-4), which are the starting compounds, can be easily synthesized by a known method.

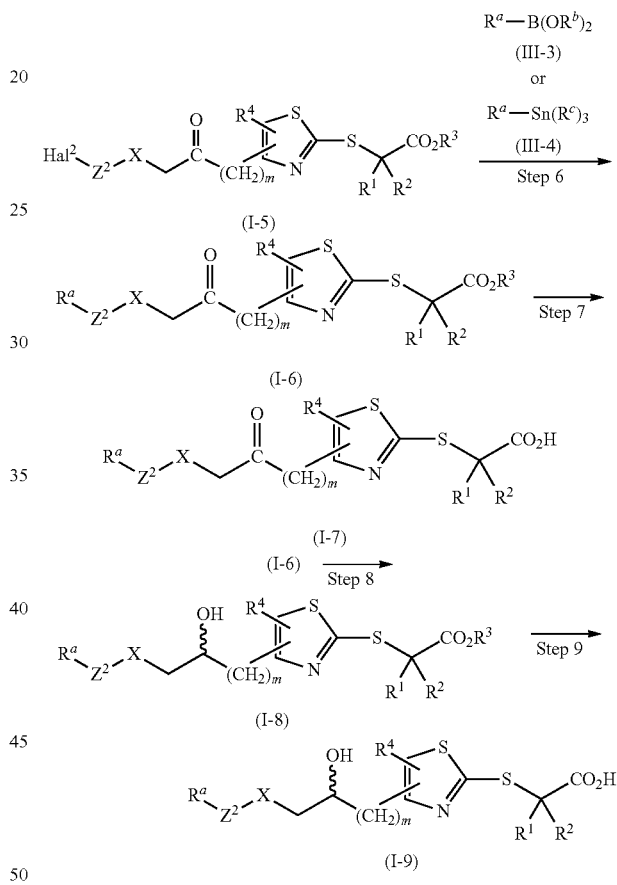

(I-5)

(I-6)

(I-7)

(I-8)

(I-9)

wherein $R^1$, $R^2$, $R^{3a}$, $R^4$, X and m are as defined above, $Z^2$ is an aryl group or a heteroaryl group, $Hal^2$ is a halogen atom or a trifluoromethanesulfonyloxy group, $R^a$ is an aryl group or a heteroaryl group, $R^b$ is a hydrogen atom or an alkyl group, or two $R^b$ form an ortho-phenylene group, an ethylene group, a 1,1,2,2-tetramethylethylene group or a 1,3-propylene group in combination, and $R^c$ is an alkyl group.

Here, examples of the "aryl group" for $Z^2$ or $R^a$ include groups similar to the "aryl group" of the "aryl group optionally having substituent(s)" for Z.

Examples of the "heteroaryl group" for $Z^2$ or $R^a$ include groups similar to the "heteroaryl group" of the "heteroaryl group optionally having substituent(s)" for Z.

Examples of the "alkyl group" for $R^b$ or $R^c$ include groups similar to the "alkyl group" of the "alkyl group optionally having substituent(s)" for $R^1$ or $R^2$.

Step 6 is generally performed in a solvent that does not adversely influence the reaction, in the presence of a metal catalyst. In this case, a base may also be added. Examples of the metal catalyst include a zerovalent palladium catalyst, a divalent palladium catalyst, a zerovalent nickel catalyst and the like. Here, examples of the zerovalent palladium catalyst include tetrakis(triphenylphosphine)palladium, tris(dibenzylideneacetone)dipalladium and the like, examples of the divalent palladium catalyst include palladium acetate, dichlorobis(triphenylphosphine)palladium and the like, and examples of the zerovalent nickel catalyst include 1,1'-bis(diphenylphosphino)ferrocenenickel and the like. In addition, to these catalysts may be added a monodentate ligand such as triphenylphosphine, tris(o-tolyl)phosphine and the like, a didentate ligand such as diphenylphosphinopropane, diphenylphosphinobutane etc. and the like. Examples of the base include alkali metal hydrogen carbonates such as sodium hydrogen carbonate and the like, alkali metal carbonates such as sodium carbonate, potassium carbonate and the like, alkali metal phosphates such as tripotassium phosphate etc. and the like. For reaction with compound (III-4), use of a base is not necessary. The amount of the metal catalyst to be used is, for example, 0.01-1 molar equivalent, preferably 0.05-0.5 molar equivalent, relative to compound (I-5). The amount of the base to be used is, for example, 1-20 molar equivalents, preferably 1-10 molar equivalents, relative to compound (I-5). The reaction temperature is generally from 0° C. to the refluxing temperature of the solvent. As the solvent that does not adversely influence the reaction, ethers such as tetrahydrofuran, dioxane and the like, aromatic hydrocarbons such as benzene, toluene and the like, amides such as N,N-dimethylformamide, N-methyl-2-pyrrolidone and the like, alcohols such as methanol, ethanol and the like, water and the like are used. These solvents may be mixed at an appropriate ratio and used in a mixture. The reaction with compound (III-4) is preferably performed in a non-aqueous solvent. The amount of compound (III-3) or compound (III-4) to be used is, for example, 1-5 molar equivalents, preferably 1-3 molar equivalents, relative to compound (I-5).

Steps 7 and 9 can be performed in the same manner as in step 2 except that compound (I-1) in step 2 of production method 1, is changed to compound (I-6) and compound (I-8), respectively.

Step 8 can be performed in the same manner as in step 4 of production method 3.

A compound represented by the formula (I-10) (hereinafter to be described as compound (I-10)), which is a compound represented by the formula (I) wherein Y moiety is —CH(OR$^{5'}$)— wherein R$^{5'}$ is an alkyl group having a carbon number of 1 to 6, and a compound represented by the formula (I-11) (hereinafter to be described as compound (I-11)) can be produced, for example, by the following method (production method 5).

[Production Method 5]

Compound (I-10) can be obtained by alkylating the hydroxyl group of compound (I-3) obtained in production method 3 (step 10). Moreover, the present compound is deesterified to give compound (I-11) (step 11).

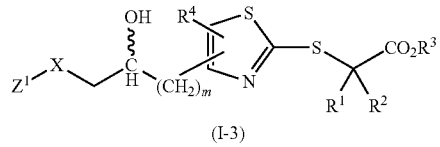

(I-3)

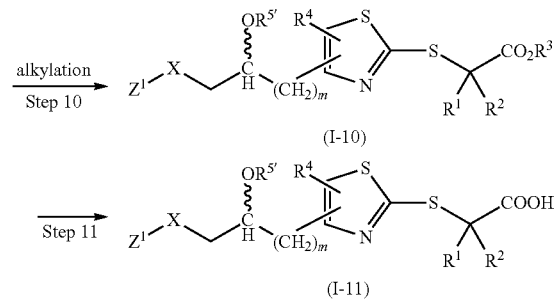

wherein R$^{5'}$ is an alkyl group, and R$^1$, R$^2$, R$^{3a}$, R$^4$, X, m and Z$^1$ are as defined above.

Examples of the "alkyl group" for R$^{5'}$ include groups similar to the "alkyl group" of the "alkyl group optionally having substituent(s)" for R$^1$ or R$^2$.

Step 10 is generally performed by reacting an alkylating agent in the presence of a base, in a solvent that does not adversely influence the reaction. As the base, metal hydrides such as sodium hydride, potassium hydride and the like, and alkali metal alkoxides such as potassium tertiary butyloxide and the like are used. The amount of the base to be used is, for example, 0.5-10 molar equivalents, preferably 1-2 molar equivalents, relative to compound (I-3). As the alkylating agent, alkyl halides such as methyliodide, ethylbromide and the like, alkyl sulfonate esters such as dimethylsulfuric acid and the like are used. The amount of the alkylating agent to be used is, for example, 0.5-10 molar equivalents, preferably 1-3 molar equivalents, relative to compound (I-3). The reaction is generally performed from −50° C. to 200° C., preferably 0° C. to 100° C. As the solvent that does not adversely influence the reaction, tetrahydrofuran, dimethylformamide, N-methylpyrrolidone and the like can be mentioned. These solvents may be mixed at an appropriate ratio and used in a mixture.

Step 11 can be performed in the same manner as in step 2 except that compound (I-1) in step 2 is changed to compound (I-10).

A compound represented by the formula (I-14) (hereinafter to be described as compound (I-14)) and a compound represented by the formula (I-15) (hereinafter to be described as compound (I-15)), which are compounds represented by the formula (I) wherein Y moiety is —CH(OH)— and optically active, can be produced, for example, by the following methods (production methods 6, 7).

[Production Method 6]

The alcohol moiety of compound (I-3) obtained in step 4 of production method 3 is converted to a compound represented by the formula (I-12) (hereinafter to be described as compound (I-12)) (step 12), which is an ester, using an optically active carboxylic acid or a derivative thereof, the obtained diastereomer mixture is resolved (step 13), and the ester is dissociated to give an optically active alcohol compound (compound represented by the formula (I-14); hereinafter to be described as compound (I-14)) (step 14). Moreover, the present compound is deesterified to give a carboxylic acid compound (compound represented by the formula (I-15); hereinafter to be described as compound (I-15)) (step 15). Step 14 and step 15 may be performed in a reverse order or performed simultaneously.

tetrahydrofuran, dioxane and the like, halogenated hydrocarbons such as chloroform, dichloromethane, dichloroethane and the like, hydrocarbons such as hexane, benzene, toluene etc. and the like are used. In addition, pyridine, which is a base, can also be used as a solvent. These solvents may be mixed at an appropriate ratio and used in a mixture. In addi-

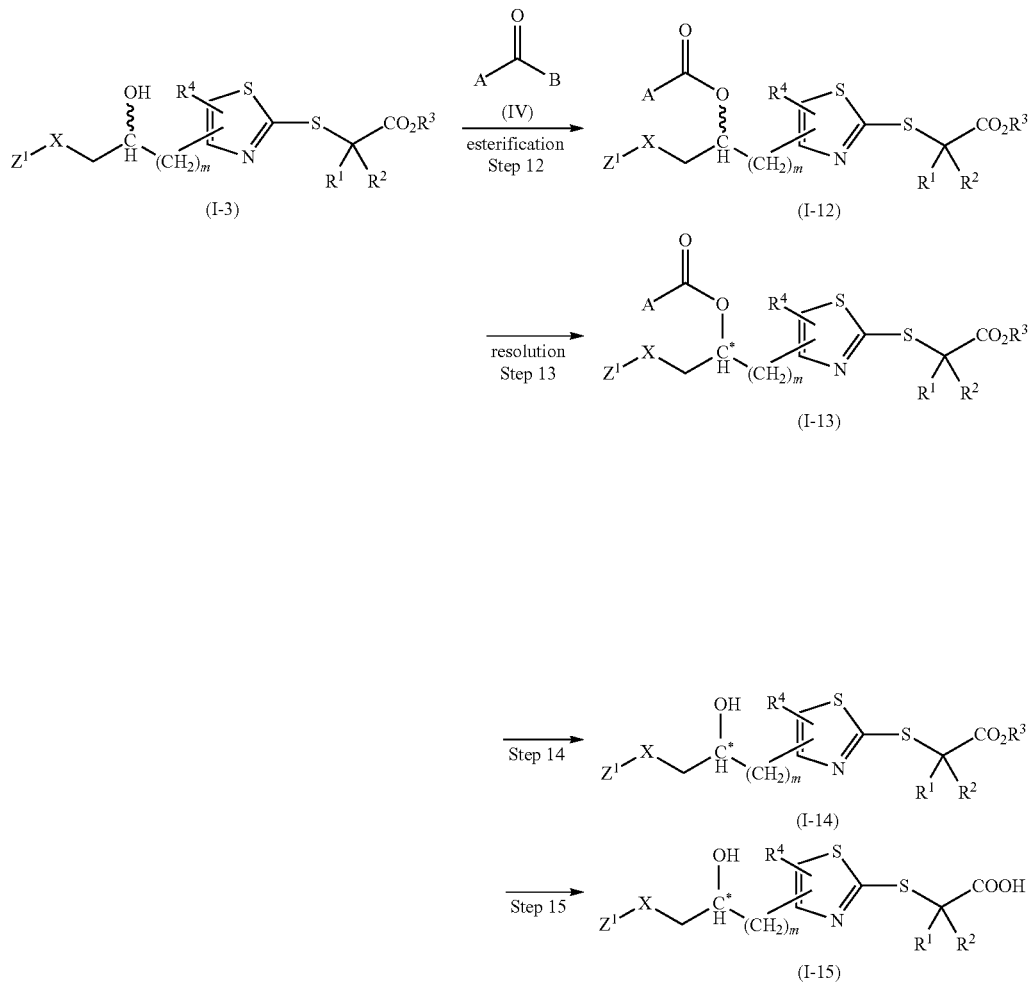

wherein $R^1$, $R^2$, $R^{3a}$, $R^4$, X, $Z^1$ and m are as defined above, a compound represented by the formula A-C(=O)—B is an optically active carboxylic acid derivative usable for esterification (hereinafter to be described as "optically active carboxylic acid derivative").

In step 12, known conditions suitable for the optically active carboxylic acid derivative to be used are selected. When, for example, acid chloride such as (+)-α-methoxy-α-trifluoromethylphenylacetyl chloride and the like is used as an optically active carboxylic acid derivative, this step is performed in the presence of a base, in a solvent that does not adversely influence the reaction. As the base in this case, organic bases such as 4-dimethylaminopyridine, pyridine, triethylamine and the like are used. The amount of the base to be used is generally 0.1-10 molar equivalents relative to compound (I-3). The reaction temperature is generally −20° C. to 100° C., preferably 0° C. to 50° C. As the solvent that does not adversely influence the reaction, ethers such as diethyl ether, tion, the amount of the derivative to be used is generally 0.1-5 molar equivalents, preferably 0.5-2 molar equivalents, relative to compound (I-3).

The resolution in step 13 can be performed by purification methods in conventional organic synthesis such as crystallization, column chromatography and the like and a combination thereof, depending on the property of compound (I-12), a diastereo mixture. Step 14 and step 15 can be performed in the same manner as in step 2, except that compound (I-1) in step 2 is changed to compound (I-13) and/or compound (I-14). Step 14 and step 15 may be performed in a reverse order or performed simultaneously.

[Production Method 7]

Compound (I-14), which is an optically active alcohol compound, can also be obtained by subjecting compound (I-1) obtained step 1 of production method 1 to an asymmetric reduction (step 16). Moreover, compound (I-14) can be converted to compound (I-15), which is a carboxylic acid compound, by deesterification (step 17).

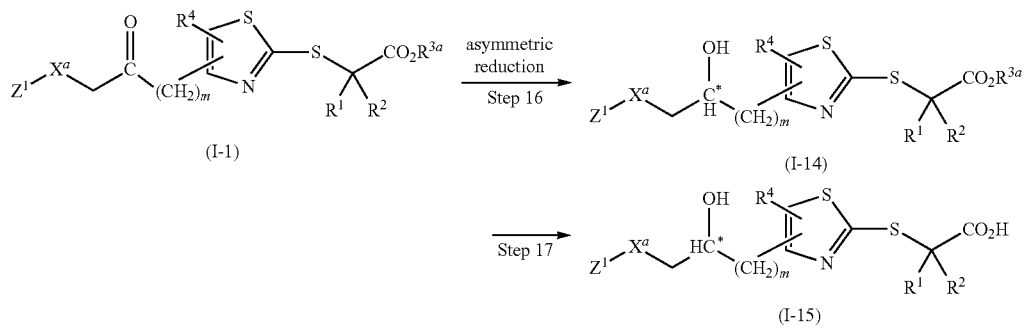

(I-1)    (I-14)    (I-15)

wherein $R^1$, $R^2$, $R^{3a}$, $R^4$, $X^a$, $Z^1$ and m are as defined above.

Step 16 can be performed by a known method of asymmetric reduction of carbonyl group described in, for example, non-patent document (The Chemical Society of Japan ed. 4th Edition Jikken Kagaku Kouza 26 organic synthesis VIII pages 23-68, 5th ed. Jikken Kagaku Kouza 19 organic compound synthesis VII, pages 65-170) and the like. For example, step 16 can be performed in a solvent that does not adversely influence the reaction, using a reducing agent and an asymmetric ligand in combination. As the reducing agent, a borane complex such as a borane-tetrahydrofuran complex, a borane-dimethylsulfide complex and the like, and the like are used. The amount of the reducing agent to be used is preferably 1-5 molar equivalents relative to compound (I-1). Examples of the asymmetric ligand include (S)-(−)-2-methyl-CBS-oxazaborolidine and the like, and the amount of use thereof is 0.001-10 molar equivalents, preferably 0.01-0.5 molar equivalents, relative to compound (I-1). The reaction temperature is generally −50-150° C., preferably −10-50° C. As the solvent that does not adversely influence the reaction, ethers such as diethyl ether, tetrahydrofuran, dioxane and the like, halogenated hydrocarbons such as chloroform, dichloromethane, dichloroethane and the like, hydrocarbons such as hexane, benzene, toluene and the like, and the like are used. These solvents may be mixed at an appropriate ratio and used in a mixture.

Step 17 can be performed in the same manner as in step 2, except that compound (I-1) in step 2 is changed to compound (I-14).

The optical purity of compound (I-15) obtained by production method 6 or 7 can be increased by a method known in conventional organic synthesis such as purification by chiral column chromatography, or conversion to a salt with an optically active organic amine such as (S) or (R)-phenylethylamine and the like and crystallization.

The following shows the representative production methods of starting compounds.

Compound (II-1) used in the above-mentioned production methods can be produced according to the method shown in the following production method 8 or 9 and using, for example, a compound having a thiol group, which is represented by the formula (V), shown below (hereinafter to be described as compound (V)) as a starting material. Compound (V) can be produced according to the method described in WO2006/049232.

[Production Method 8]

Haloketone (II-1) can be obtained by halomethylation of compound (V), which is a carboxylic acid. (step 18)

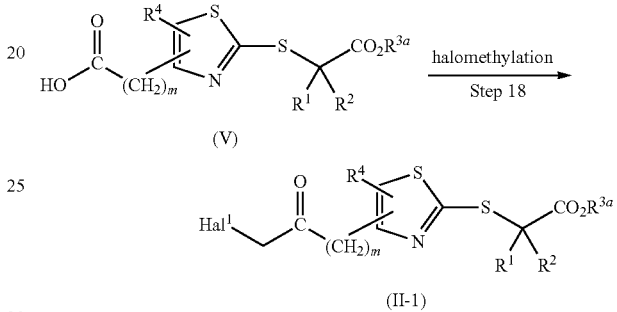

(V)

(II-1)

wherein $R^1$, $R^2$, $R^{3a}$, $R^4$, $Hal^1$ and m are as defined above.

Step 18 can be performed by a known method, for example, the method via diazoketone, which is described in non-patent document (J. Org. Chem. 20 (1955), 38); the method including reacting an ester obtained from carboxylic acid with dihalomethane in the presence of a base such as lithium diisopropylamide and the like, which is described in non-patent document (Tetrahedron Lett. 42 (2001), 5887); the method including reacting an ester obtained from carboxylic acid with halomethyllithium, which is described in non-patent document (J. Chem. Soc. Chem. Commun. 1994, 969); the method including reacting an ester obtained from carboxylic acid with metal enolate prepared from haloacetic acid or a salt thereof, followed by decarboxylation, which is described in patent document (WO96/23756) and the like.

The reaction of metal enolate prepared from haloacetic acid or a salt thereof can be performed by adding haloacetic acid or a salt thereof, Grignard reagent such as n-butylmagnesium chloride and the like, and diisopropylamine to a lower alkyl ester such as methyl or ethyl ester and the like that can be easily synthesized from compound (V) by a method known from documents. The amount thereof to be used can be appropriately determined by those of ordinary skill in the art. The reaction can be generally performed in a solvent not influential on the reaction, at −50° C. to 100° C., preferably −10° C. to 50° C. As the solvent not influential on the reaction includes, for example, ethers such as tetrahydrofuran, diethyl ether and the like.

[Production Method 9]

A compound represented by the formula (VI) (hereinafter to be described as compound (VI)) is produced from compound (V) (step 19), and the compound is halogenated to give haloketone (II-1) (step 20).

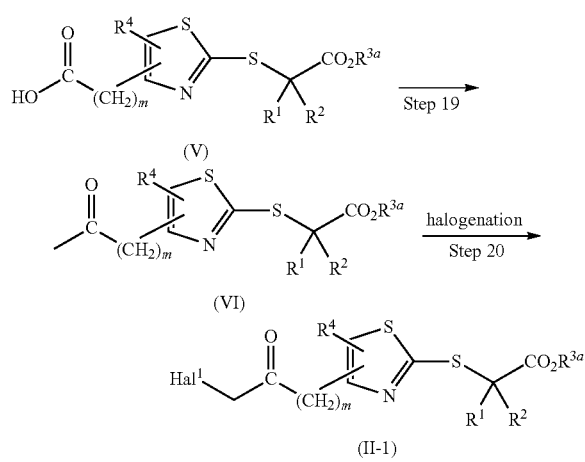

wherein $R^1$, $R^2$, $R^{3a}$, $R^4$, $Hal^1$ and m are as defined above.

Step 19 can be performed, for example, reacting compound (V), which is a carboxylic acid, or a suitable derivative thereof with an organic metal reagent. Examples of the suitable derivative include hydroxamic acid ester and the like that can be synthesized by a known method. Examples of the organic metal reagent include Grignard reagents such as methylmagnesium bromide and the like and alkyllithium reagents such as methyllithium and the like. The amount of the organic metal reagent to be used is generally 1-10 molar equivalents, preferably 3-5 molar equivalents, relative to compound (V) or a suitable derivative thereof. The reaction can be performed in a solvent that does not adversely influence the reaction, generally at −50° C. to 100° C., preferably −20° C. to 30° C. As the solvent that does not adversely influence the reaction, ethers such as tetrahydrofuran, diethyl ether and the like can be mentioned.

Step 20 can be performed in the presence of a halogenating agent such as phenyltrimethylammonium tribromide and the like, in a solvent that does not adversely influence the reaction, generally at −50° C. to 100° C., preferably −10° C. to 40° C. As the solvent that does not adversely influence the reaction, ethers such as tetrahydrofuran, diethyl ether and the like, halogenated hydrocarbons such as chloroform, carbon tetrachloride and the like can be mentioned. The amount of the halogenating agent to be used is generally 0.5-5 molar equivalents, preferably 0.9-2 molar equivalents, relative to the compound.

A compound wherein Z is a cycloalkyl group, an arylalkyl group, an aryloxyalkyl group or a heteroaryl group can also be produced in the same manner by the above-mentioned method.

The thus-produced compound (I) of the present invention can be appropriately treated by a known separation and purification procedure, for example, concentration, extraction, chromatography, reprecipitation, recrystallization and the like to have any purity.

The thus-produced compound (I) can be converted to a salt thereof, where necessary, by treating with an inorganic acid such as hydrochloric acid, hydrobromic acid and the like, an organic acid such as trifluoroacetic acid, acetic acid, methanesulfonic acid, benzenesulfonic acid and the like, an alkali metal such as sodium, potassium, calcium and the like, an organic base such as dicyclohexylamine and the like, an amino acid such as lysine, arginine and the like.

The compound (I) of the present invention is effective for the prophylaxis and/or treatment of hyperlipidemia, arteriosclerosis and ischemic cardiac diseases, and useful as a highly safe prophylaxis and/or therapeutic drug for hyperlipidemia.

Furthermore, the compound (I) of the present invention is also useful as a prophylactic and/or therapeutic drug for hyperlipidemia secondary to diabetes. The hyperlipidemia secondary to diabetes refers to hyperlipidemia concurrently developed by diabetic patients, and is sometimes referred to as diabetic hyperlipidemia.

In the present specification, the "pathology of diabetic patients who developed hyperlipidemia secondary to diabetes" refers to the pathology where a blood glucose level-improving effect is observed by a diabetes treatment, but TG value, LDL-C value, HDL-C value and the like are not normal. The medicament of the present invention can be applied to such pathologies for the treatment purposes. It is also possible to apply the medicament of the present invention for the purposes of treatment of or prophylaxis in diabetes patients or patients with the risk of recurrence thereof, who show TG value, LDL-C value, HDL-C value and the like within the normal value ranges.

In the present specification, the "patients who developed hyperlipidemia secondary to diabetes" refers to patients showing a blood glucose level-improving effect by a diabetes treatment but TG value, LDL-C value, HDL-C value and the like outside the normal values. The medicament of the present invention can be administered to such patients.

A WHO classification classifying hyperlipidemia based on lipoprotein phenotype is known. A phenotype showing high triglyceride level includes type I hyperlipidemia, IIb-type hyperlipidemia, type III hyperlipidemia, type IV hyperlipidemia, type V hyperlipidemia and the like. Among such types, individuals strongly suspected of having diabetes, who show particularly high serum TG level and/or low HDL level, and individuals having an undeniable possibility of diabetes are effective application subjects of the medicament of the present invention. Needless to say, the medicament of the present invention can also be applied to patients belonging to other classification and diagnosed with hyperlipidemia secondary to diabetes. Moreover, it is possible to apply the medicament of the present invention for the purposes of treatment of or prophylaxis in diabetes patients or patients with the risk of recurrence thereof, who show TG value, LDL-C value, HDL-C value and the like within the normal value ranges.

Furthermore, the compound (I) of the present invention can also be used as a prophylactic and/or therapeutic drug for diabetes.

Here, diabetes means a fasting blood sugar level of not less than 126 mg/dL, or a 75 g glucose loading test 2 hr value of not less than 200 mg/dL. In addition, a casual blood glucose level of not less than 200 mg/dL is also included in diabetes.

The compound of the present invention (I) can be administered to a single subject simultaneously with other antihyperlipemia agent and the like, or in a staggered manner. As antihyperlipemia agent, statin compounds that are cholesterol synthase inhibitors, squalene synthase inhibitors, fibrate compounds having a triglyceride lowering action, and the like can be mentioned. When the compound of the present invention is used in combination with multiple agents, the mixing ratio thereof can be appropriately determined according to the administration subject, age and body weight of administration subject, symptom, administration time, dosage form, administration method, combination and the like.

A preferable compound of the present invention, particularly, the compound of Example 12, is not involved in the metabolism by CYP, and therefore, a combined use with a medicament (e.g., fluvastatin etc.) involved in the metabolism by CYP is available. Thus, it can be a highly safe, superior prophylactic or therapeutic drug for hyperlipidemia and the like.

When the compound (I) of the present invention or an acid addition salt thereof is used as the aforementioned medicament, it can be orally or parenterally administered as it is or in the form of a powder, granule, tablet, capsule, injection and the like after mixing with an appropriate pharmaceutically acceptable carrier. Examples of the pharmaceutically acceptable carrier include diluent, binder (syrup, gum arabic, gelatin, sorbit, tragacanth, polyvinylpyrrolidone), excipient (lactose, sucrose, cornstarch, potassium phosphate, sorbit, glycine), lubricant (magnesium stearate, talc, polyethylene glycol, silica), disintegrant (potato starch) and wetting agent (sodium lauryl sulfate) and the like. The above-mentioned preparation contains an effective amount of compound (I) or a pharmaceutically acceptable salt thereof.

The dose of the compound (I) of the present invention or a pharmaceutically acceptable salt thereof varies depending on the administration route, target disease, symptom, body weight and age of patients, and the compound to be used, and can be appropriately determined according to the purpose of administration. Generally, for oral administration to an adult, it is preferably administered at 0.01-1000 mg/kg body weight/day, preferably 0.05-500 mg/kg body weight/day, in one to several portions per day.

EXAMPLES

The present invention is explained in detail in the following by referring to Examples, which are not to be construed as limitative.

The chemical shift of $^1$H-NMR is shown by parts per million (ppm) of relative delta ($\delta$) value, using tetramethylsilane (TMS) as the internal standard. The coupling constant is shown in hertz (Hz), and the obvious multiplicity is shown by s (singlet), d (doublet), t (triplet), q (quartet), quint (quintet), m (multiplet), dd (doublet of doublets), td (triplet of doublets), brs (broad singlet) and the like. The mass spectrometry results show $(M+H)^+$ values by high performance liquid chromatography mass spectrometry method (electrospray method).

Example 1

2-{[4-(chloroacetyl)-1,3-thiazol-2-yl]thio}-2-methylpropionic acid tert-butyl ester

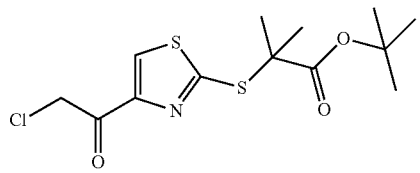 [SMILES: CC(C)(C)OC(=O)C(C)(C)Sc1nc(C(=O)CCl)cs1]

2-(1-tert-Butoxycarbonyl-1-methyl-ethylsulfanyl)-thiazole-4-carboxylic acid was dissolved in methylene chloride (1200 mL), 1-ethyl-3-(3-dimethylaminopropyl)carbodiimide hydrochloride (191.70 g), 4-dimethylaminopyridine (5.86 g) and methanol (19.47 mL) were added and the mixture was stirred at room temperature overnight. The mixture was washed with dilute hydrochloric acid (about 0.5 mol/L), saturated aqueous sodium hydrogen carbonate solution, and saturated aqueous sodium chloride solution (each 500 mL), and dried over anhydrous sodium sulfate. The solvent was evaporated and the residue was dissolved again in ethyl acetate (700 mL), washed successively with dilute hydrochloric acid (about 0.2 mol/L), saturated aqueous sodium hydrogen carbonate solution, and saturated aqueous sodium chloride solution (each 300 mL), and dried over anhydrous sodium sulfate. The solvent was evaporated and the obtained solid was washed with a mixed solvent (10:1, about 500 mL) of hexane and ethyl acetate, and the solid was collected by filtration. The solvent was evaporated from the filtrate and the residue was purified by silica gel column chromatography (using 500 g of Fuji Silysia BW-300, elution solvent: hexane/ethyl acetate=3/1). The obtained solid was washed with hexane and combined with the solid obtained earlier to give 2-(1-tert-butoxycarbonyl-1-methyl-ethylsulfanyl)-thiazole-4-carboxylic acid methyl ester (94.6 g).

To a mixed solution of diisopropylamine (75 mL) and THF 100 mL was added dropwise n-butylmagnesium chloride (2 M, THF solution, 250 g), and the mixture was stirred in a hot-water bath at 40° C. for 2 hr 10 min (SOLUTION A). Separately, 2-(1-tert-butoxycarbonyl-1-methyl-ethylsulfanyl)-thiazole-4-carboxylic acid methyl ester (39.04 g) obtained earlier and chloroacetic acid (17.43 g) were dissolved in THF 150 mL, and the mixture was stirred under ice-cooling for 1 hr (SOLUTION B). SOLUTION A prepared earlier was added dropwise over 10 min to SOLUTION B. After the completion of the dropwise addition, ice bath was removed, and the mixture was further stirred for 1 hr. The reaction solution was ice-cooled again, 1N aqueous hydrochloric acid was added to adjust pH of the solution to about 3. The mixture was extracted with ethyl acetate (500 mL and 200 mL), washed successively with saturated aqueous sodium hydrogen carbonate solution (300 mL, twice), and saturated aqueous sodium chloride solution (300 mL), and dried over anhydrous sodium sulfate. The solvent was evaporated, and the residue was purified by column chromatography (first, Fuji Silysia BW-300 (500 g) was used to remove highly-polar components; thereafter, purified twice by using Moritex Corporation Purif Pack SI of 60 µm, size 200, elution solvent: hexane/ethyl acetate=95/5→65/35) to give the title compound as a brown oily substance (12.38 g). A similar operation was performed once more at the same scale to give the object product (11.49 g).

$^1$H-NMR (CDCl$_3$, 300 MHz)
δ: 1.45 (9H, s), 1.66 (6H, s), 4.88 (2H, s), 8.26 (1H, s).
LC-MS: 280 (M-tBu+H)$^+$

Example 2

2-[(4-{2-[(4'-fluorobiphenyl-4-yl)oxy]-1-hydroxyethyl}-1,3-thiazol-2-yl)thio]-2-methylpropionic acid Example 2-1

2-[(4-{[(4'-fluorobiphenyl-4-yl)oxy]acetyl}-1,3-thiazol-2-yl)thio]-2-methylpropionic acid tert-butyl ester

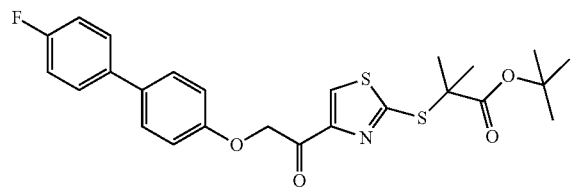 [SMILES: CC(C)(C)OC(=O)C(C)(C)Sc1nc(C(=O)COc2ccc(-c3ccc(F)cc3)cc2)cs1]

2-{[4-(Chloroacetyl)-1,3-thiazol-2-yl]thio}-2-methylpropionic acid tert-butyl ester (23.8 g) and 4'-fluorobiphenyl-4-ol (12.00 g) obtained in Example 1 were dissolved in toluene (650 mL), aqueous sodium hydroxide solution (1 mol/L, 71 mL), tetrabutylammonium iodide (2.62 g) and water (71 mL) were added, and the mixture was heated under reflux for 3 hr, and allowed to cool to perform partitioning. The organic layer was washed twice with 1 mol/L aqueous sodium hydroxide solution (300 mL) and twice with saturated aqueous sodium chloride solution (200 mL), and dried over anhydrous sodium sulfate. The solvent was evaporated and the obtained residue was purified by column chromatography (Moritex Purif Pack SI 60 µm size 200 was used. elution solvent: hexane/ethyl acetate=95/5→70/30) to give the title compound as a pale-yellow oily substance (1.128 g).

$^1$H-NMR (CDCl$_3$, 300 MHz)

δ: 1.43 (9H, s), 1.68 (6H, s), 5.45 (2H, s), 6.91-7.13 (4H, m), 7.45-7.51 (4H, m), 8.29 (1H, s).

LC-MS: 432 (M-tBu+H)$^+$

Example 2-2

2-[(4-{2-[(4'-fluorobiphenyl-4-yl)oxy]-1-hydroxyethyl}-1,3-thiazol-2-yl)thio]-2-methylpropionic acid tert-butyl ester

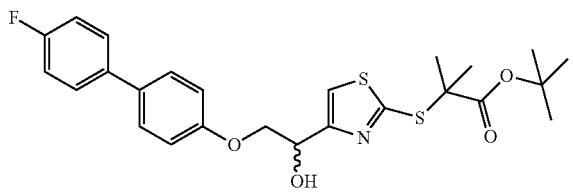 [SMILES: CC(C)(C)OC(=O)C(C)(C)Sc1nc(C(O)COc2ccc(-c3ccc(F)cc3)cc2)cs1]

2-[(4-{[(4'-Fluorobiphenyl-4-yl)oxy]acetyl}-1,3-thiazol-2-yl)thio]-2-methylpropionic acid tert-butyl ester 967 mg obtained in Example 2-1 was dissolved in ethanol (10 mL) and, under ice-cooling, sodium borohydride (75 mg) was added and the mixture was stirred for 2 hr 30 min. Water (10 mL) was added, pH was adjusted to about 3 with aqueous hydrochloric acid (1 mol/L), and the mixture was extracted with ethyl acetate (50 mL). The organic layer was washed with saturated aqueous sodium chloride solution, and dried over anhydrous sodium sulfate. The solvent was evaporated and the obtained residue purified by column chromatography (Moritex Corporation Purif Pack SI 60 µm size 200 was used. elution solvent: hexane/ethyl acetate=9/1→6/4) to give the title compound as a pale-yellow oily substance (907 mg).

$^1$H-NMR (CDCl$_3$, 300 MHz)

δ: 1.43 (9H, s), 1.59 (6H, s), 2.99 (1H, d, J=4.5 Hz), 4.19 (1H, dd, J=7.5 Hz, 9.6 Hz), 4.42 (1H, d, J=3.9 Hz, 9.6 Hz), 5.25 (1H, m), 6.99 (2H, d, J=6.6 Hz), 7.10 (2H, t, J=6.9 Hz), 7.42-7.51 (5H, m).

LC-MS: 490 (M+H)$^+$

Example 2-3

2-[(4-{2-[(4'-fluorobiphenyl-4-yl)oxy]-1-hydroxyethyl}-1,3-thiazol-2-yl)thio]-2-methylpropionic acid

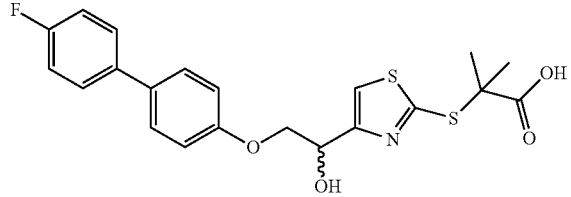 [SMILES: CC(C)(Sc1nc(C(O)COc2ccc(-c3ccc(F)cc3)cc2)cs1)C(=O)O]

2-[(4-{2-[(4'-Fluorobiphenyl-4-yl)oxy]-1-hydroxyethyl}-1,3-thiazol-2-yl)thio]-2-methylpropionic acid tert-butyl ester (877 mg) obtained in Example 2-2 was dissolved in methylene chloride (3 mL), trifluoroacetic acid (3 mL) was added and the mixture was stirred at room temperature overnight. The solvent was evaporated and the obtained residue was dissolved in ethyl acetate (30 mL), washed successively with water and saturated aqueous sodium chloride solution, and dried over anhydrous sodium sulfate. The solvent was evaporated and the obtained residue was applied to column chromatography (Moritex Corporation Purif Pack SI 60 µm size 200 was used. elution solvent: hexane/ethyl acetate=7/3→0/10). The solvent was evaporated from the obtained fraction containing the object product to give a white solid. This was dissolved in a mixed solvent of hexane and ethyl acetate with heating, and the mixture was cooled to allow precipitation of a solid to give the title compound (450.6 mg).

$^1$H-NMR (CDCl$_3$, 300 MHz)

δ: 1.61 (3H, s), 1.64 (3H, s), 4.23 (1H, dd, J=6.8 Hz, 9.6 Hz), 4.39 (1H, dd, J=3.72 Hz, 9.6 Hz), 5.26 (1H, m), 6.97 (2H, d, J=8.8 Hz), 7.10 (2H, t, J=8.8 Hz), 7.43-7.50 (5H, m).

LC-MS: 434 (M+H)$^+$

Example 3

2-[(4-{[(4'-fluorobiphenyl-4-yl)oxy]acetyl}-1,3-thiazol-2-yl)thio]-2-methylpropionic acid

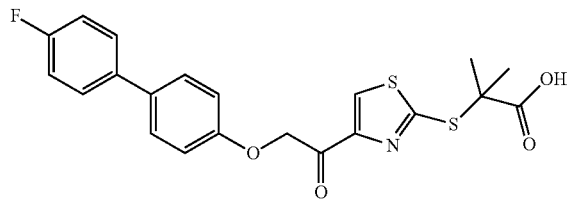 [SMILES: CC(C)(Sc1nc(C(=O)COc2ccc(-c3ccc(F)cc3)cc2)cs1)C(=O)O]

By an operation similar to that in Example 2-3 and using 2-[(4-{[(4'-fluorobiphenyl-4-yl)oxy]acetyl}-1,3-thiazol-2-yl)thio]-2-methylpropionic acid tert-butyl ester (124 mg) obtained in Example 2-1, the title compound (69 mg) was obtained.

$^1$H-NMR (CDCl$_3$, 300 MHz)

δ: 1.69 (6H, s), 5.35 (2H, s), 7.01 (2H, d, J=8.7 Hz), 7.09 (2H, t, J=8.7 Hz), 7.44-7.50 (4H, m), 8.25 (1H, s).

LC-MS: 432 (M+H)$^+$

Example 4

2-[(4-{[(4'-chlorobiphenyl-4-yl)oxy]acetyl}-1,3-thiazol-2-yl)thio]-2-methylpropionic acid

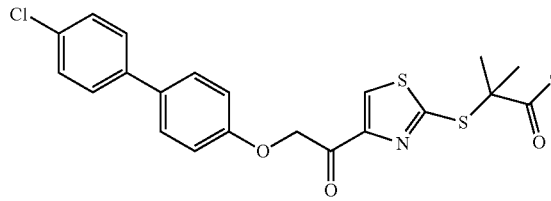

By an operation similar to that in Example 2-1 and using 2-{[4-(chloroacetyl)-1,3-thiazol-2-yl]thio}-2-methylpropionic acid tert-butyl ester (561 mg) obtained in Example 1 and 4'-chlorobiphenyl-4-ol (307 mg), 2-[(4-{[(4'-chlorobiphenyl-4-yl)oxy]acetyl}-1,3-thiazol-2-yl)thio]-2-methylpropionic acid tert-butyl ester (129 mg) was obtained. Furthermore, by operations similar to those in Example 2-2 and 2-3, the title compound (36 mg) was obtained.

$^1$H-NMR (CDCl$_3$, 300 MHz)

δ: 1.70 (6H, s), 5.36 (2H, s), 7.04 (2H, d, J=8.7 Hz), 7.37 (2H, d, J=8.7 Hz), 7.44-7.50 (4H, m), 8.26 (1H, s).

LC-MS: 446 (M+H)$^+$

Example 5

2-[(4-{2-[(4'-chlorobiphenyl-4-yl)oxy]-1-hydroxyethyl}-1,3-thiazol-2-yl)thio]-2-methylpropionic acid

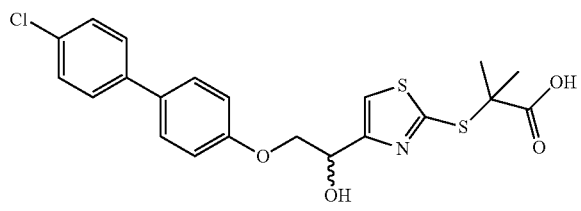 [SMILES: CC(C)(Sc1nc(C(O)COc2ccc(-c3ccc(Cl)cc3)cc2)cs1)C(=O)O]

By an operation similar to that in Example 2-1 and using 2-{[4-(chloroacetyl)-1,3-thiazol-2-yl]thio}-2-methylpropionic acid tert-butyl ester (1.49 g) obtained in Example 1 and 4'-chlorobiphenyl-4-ol (772 mg), 2-[(4-{[(4'-chlorobiphenyl-4-yl)oxy]acetyl}-1,3-thiazol-2-yl)thio]-2-methylpropionic acid tert-butyl ester (864 mg) was obtained. By successive operations similar to those in Example 2-2 and 2-3 using 568 mg thereof, the title compound (299 mg) was obtained.

$^1$H-NMR (CDCl$_3$, 300 MHz)

δ: 1.61 (3H, s), 1.64 (3H, s), 4.24 (1H, dd, J=6.8 Hz, 9.5 Hz), 4.39 (1H, dd, J=3.72 Hz, 9.6 Hz), 5.27 (1H, m), 6.99 (2H, d, J=8.7 Hz), 7.36-7.49 (6H, m).

LC-MS: 450 (M+H)$^+$

Example 6

2-[(4-{2-[(4'-fluorobiphenyl-4-yl)oxy]-1-methoxyethyl}-1,3-thiazol-2-yl)thio]-2-methylpropionic acid

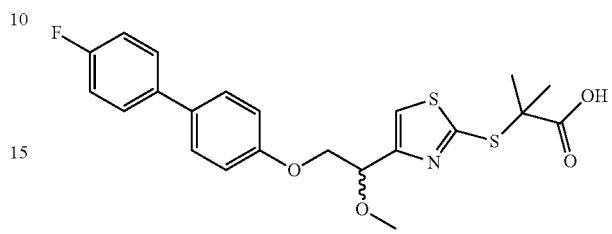

Sodium hydride (60% oil suspension, 24 mg) was suspended in DMF (5 mL), and a solution of 2-[(4-{2-[(4'-fluorobiphenyl-4-yl)oxy]-1-hydroxyethyl}-1,3-thiazol-2-yl)thio]-2-methylpropionic acid tert-butyl ester (331 mg) obtained in Example 2-2 in DMF (1.5 mL) was added. After cease of foaming, methyl iodide (0.12 mL) was added, and the mixture was stirred at room temperature for 30 min. Water (20 mL) was added, and the mixture was stirred, extracted with ethyl acetate (50 mL), washed with saturated brine, and dried over anhydrous sodium sulfate. The solvent was evaporated, and the residue was purified by column chromatography (Fuji Silysia silica gel BW300 was used. elution solvent: hexane/ethyl acetate-9/1-7/3) to give tert-butyl ester of the title compound (222 mg). By an operation similar to that in Example 2-3 and using the compound, the title compound (177 mg) was obtained.

$^1$H-NMR (CDCl$_3$, 300 MHz)

δ: 1.61 (3H, s), 1.64 (3H, s), 3.51 (3H, s), 4.32 (1H, d, J=5.1 Hz), 4.81 (1H, t, J=8.6 Hz), 6.96 (2H, d, J=8.7 Hz), 7.08 (2H, t, J=8.6 Hz), 7.38-7.50 (5H, m).

LC-MS: 448 (M+H)$^+$

Example 7

2-{[4-(2-{[5-(4-fluorophenyl)pyridin-2-yl]oxy}-1-hydroxyethyl)-1,3-thiazol-2-yl]thio}-2-methylpropionic acid

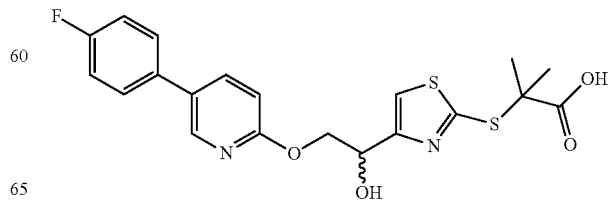

Example 7-1

2-[(4-{[(5-bromopyridin-2-yl)oxy]-acetyl}-1,3-thiazol-2-yl)thio]-2-methylpropionic acid tert-butyl ester

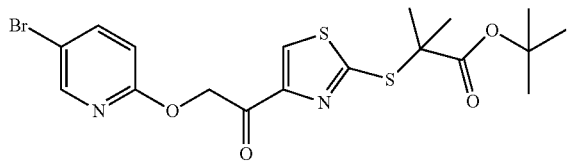 [SMILES: CC(C)(C)OC(=O)C(C)(C)Sc1nc(C(=O)COc2ccc(Br)cn2)cs1]

5-Bromo-2-hydroxypyridine (1.795 g) was dissolved in methanol (60 mL), a solution of silver nitrate (1.752 g) in water (40 mL) was added and the mixture was stirred. Aqueous ammonia was added, and the precipitate was collected by filtration to give 5-bromo-2-hydroxypyridine silver salt (2.68 g). The salt (2.37 g) and 2-{[4-(chloroacetyl)-1,3-thiazol-2-yl]thio}-2-methylpropionic acid tert-butyl ester (2.364 g) obtained in Example 1 were dissolved in ethanol (50 mL), and the mixture was stirred for 46 hr with heating under reflux. The reaction mixture was filtered through celite and the solvent was evaporated. The residue was dissolved again in ethyl acetate (100 mL), and the mixture was washed successively with 0.5 mol/L aqueous hydrochloric acid and saturated brine, and dried over anhydrous sodium sulfate. The solvent was evaporated, and the residue was purified by column chromatography (Yamazen HI-FLASH™ COLUMN size 3 L, elution solvent: hexane/ethyl acetate=9/1-6/4) to give the title compound (247 mg).

$^1$H-NMR (CDCl$_3$, 300 MHz)
δ: 1.43 (9H, s), 1.68 (6H, s), 5.67 (2H, s) 6.85 (1H, d, J=8.6 Hz), 7.69 (1H, d d, J=2.4 Hz, 8.6 Hz), 8.05 (1H, d, J=2.4 Hz), 8.21 (1H, s).

Example 7-2

2-{[4-(2-{[5-(4-fluorophenyl)pyridin-2-yl]oxy}-1-hydroxyethyl)-1,3-thiazol-2-yl]thio}-2-methylpropionic acid

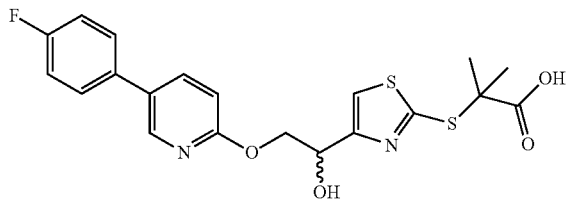 [SMILES: CC(C)(Sc1nc(C(O)COc2ccc(-c3ccc(F)cc3)cn2)cs1)C(=O)O]

2-[(4-{[(5-Bromopyridin-2-yl)oxy]-acetyl}-1,3-thiazol-2-yl)thio-2-methylpropionic acid tert-butyl ester (242 mg) obtained in Example 7-1 was dissolved in THF (2 mL), 4-fluorophenylboric acid (107 mg), tetrakis(triphenylphosphine)palladium (58 mg) and 2 mol/L aqueous sodium carbonate solution (2 mL) were added, and the mixture was stirred for 3.5 hr with heating under reflux. Water and ethyl acetate were added to the reaction mixture. The mixture was stirred, partitioned, and the ethyl acetate layer was washed with saturated aqueous sodium chloride solution, and dried over anhydrous sodium sulfate. The solvent was evaporated, and the obtained residue was purified by column chromatography (Yamazen HI-FLASH™ COLUMN size 2 L, elution solvent: hexane/ethyl acetate=9/1-6/4) to give 2-{[4-(2-{[5-(4-fluorophenyl)pyridin-2-yl]oxy}-1-acetyl)-1,3-thiazol-2-yl]thio}-2-methylpropionic acid tert-butyl ester (140 mg). By successive operations similar to those in Example 2-2 and 2-3 using the compound, the title compound (58 mg) was obtained.

$^1$H-NMR (CDCl$_3$, 300 MHz)
δ: 1.66 (6H, s), 4.68 (1H, dd, J=6 Hz, 12.3 Hz), 4.78 (1H, dd, J=2.4 Hz, 12 Hz), 5.26 (1H, m), 6.86 (1H, d, J=8.4 Hz), 7.15 (2H, t, J=8.7 Hz), 7.38 (1H, s), 7.44-7.49 (2H, m), 7.79 (1H, dd, J=2.7 Hz, 9 Hz), 8.29 (1H, d, J=2.7 Hz).
LC-MS: 435 (M+H)$^+$

Example 8

2-{[4-acetyl-1,3-thiazol-2-yl]thio}-2-methylpropionic acid tert-butyl ester

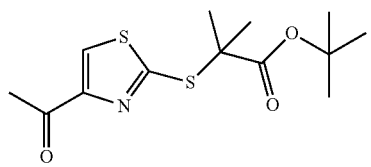 [SMILES: CC(=O)c1csc(SC(C)(C)C(=O)OC(C)(C)C)n1]

2-(1-tert-Butoxycarbonyl-1-methyl-ethylsulfanyl)-1,3-thiazole-4-carboxylic acid (30.34 g), 1-ethyl-3-(3-dimethylaminopropyl)carbodiimide hydrochloride (19.17 g) and 1-hydroxybenzotriazole (13.35 g) were dissolved in dimethylformamide (550 ml) under ice-cooling, and the mixture was warmed to room temperature and stirred for 1 hr 30 min. Separately, N,O-dimethylhydroxylamine hydrochloride (14.63 g) was suspended in tetrahydrofuran (50 mL), 20% aqueous potassium carbonate solution (50 mL) was added to convert same to a free amine and partitioned. The organic layer was dried over sodium sulfate. The solution after removal of desiccant was added to the dimethylformamide reaction mixture above, and the mixture was stirred at room temperature overnight. To the reaction mixture was added water (500 mL) and the mixture was stirred, and extracted twice with ethyl acetate (500 mL). The extract was washed successively with saturated aqueous sodium hydrogen carbonate solution and saturated aqueous sodium chloride solution (each 500 mL), and dried over anhydrous sodium sulfate. The desiccant was removed, the solvent was evaporated, and the obtained residue was purified by column chromatography (Yamazen HI-FLASH™ COLUMN size 3 L, elution solvent: hexane/ethyl acetate=4/1-5/5, performed twice) to give 2-[(4-{[methoxy(methyl)amino]carbonyl}-1,3-thiazol-2-yl)thio]-2-methylpropionic acid tert-butyl ester (32.56 g). 30.54 g of this compound was dissolved in tetrahydrofuran (400 mL), and methylmagnesium bromide (1.4 mol/L, toluene/tetrahydrofuran=75/25 solution) (68 mL) was added dropwise over 30 min under ice-cooling. After 1 hr 25 min, methyl magnesium bromide solution (5 mL) was added, and the mixture was stirred for 1 hr 10 min. The disappearance of the starting materials was confirmed by thin layer chromatography, 0.5 mol/L aqueous hydrochloric acid (200 mL) was added, the mixture was stirred and extracted with ethyl acetate (500 mL). The organic layer was washed successively with saturated aqueous sodium hydrogen carbonate solution, and saturated aqueous sodium chloride solution (each 200 mL), and dried over anhydrous sodium sulfate. The solvent was evaporated and the obtained residue was purified by column chromatography (Yamazen HI-FLASH™ COLUMN size 3 L, elution solvent: hexane/ethyl acetate=95/5-50/50, performed 3 times) to give the title compound (21.89 g).
¹H-NMR (CDCl₃, 300 MHz)
δ: 1.43 (9H, s), 1.71 (6H, s), 2.66 (3H, s), 8.13 (1H, s).
LC-MS: 301 (M+H)⁺

Example 9

2-{[4-bromoacetyl-1,3-thiazol-2-yl]thio}-2-methylpropionic acid tert-butyl ester

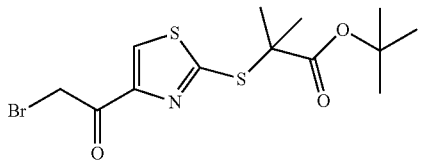 [SMILES: CC(C)(C)OC(=O)C(C)(C)Sc1nc(C(=O)CBr)cs1]

2-{[4-Acetyl-1,3-thiazol-2-yl]thio}-2-methylpropionic acid tert-butyl ester (15.90 g) obtained in Example 8 was dissolved in tetrahydrofuran (150 mL), phenyltrimethylammonium tribromide (21.81 g) was added by small portions over 15 min, and the mixture was stirred at room temperature overnight. The precipitated solid was filtered off, the solvent was evaporated, and the residue was dissolved in ethyl acetate (200 mL). The solution was washed successively with water and saturated aqueous sodium chloride solution (each 100 mL) and dried over anhydrous sodium sulfate. The solvent was evaporated and the obtained residue was purified by column chromatography (Yamazen HI-FLASH™ COLUMN size 3 L, elution solvent: hexane/ethyl acetate-90/10-50/50, performed in 5 times) to give the title compound (12.28 g).
¹H-NMR (CDCl₃, 300 MHz)
δ: 1.43 (9H, s), 1.63 (6H, s), 4.69 (2H, s), 8.26 (1H, s).
LC-MS: 324 (M-tBu+H)⁺

Example 10

2-[(4-{(1S)-2-[(4'-fluorobiphenyl-4-yl)oxy]-1-hydroxyethyl}-1,3-thiazol-2-yl)thio]-2-methylpropionic acid Example 10-1

2-[(4-{[(4'-fluorobiphenyl-4-yl)oxy]acetyl}-1,3-thiazol-2-yl)thio]-2-methylpropionic acid tert-butyl ester The bromoketone compound (10.462 g) obtained in Example 9 was dissolved in acetone (300 mL), 4'-fluorobiphenyl-4-ol (5.17 g) and potassium carbonate (3.80 g) were added and the mixture was heated under reflux for 6 hr 20 min. The solid was filtered off, and the solvent of the filtrate was evaporated. The residue was dissolved in toluene (100 mL), washed 3 times with aqueous sodium hydroxide solution (1 mol/L) (50 mL), washed with saturated brine (50 mL), and dried over anhydrous sodium sulfate. The solvent was evaporated and the residue was purified by column chromatography (divided in 3 times. Moritex Corporation purif Pack™ Si 60 μm, size 200 was used. eluent: hexane/ethyl acetate=90/10-60/40) to give the title compound (7.36 g).
¹H-NMR (CDCl₃, 300 MHz)
δ: 1.43 (9H, s), 1.68 (6H, s), 5.4 (2H, s), 7.00-7.13 (4H, m), 7.45-7.55 (4H, m), 8.29 (1H, s).

Example 10-2

2-[(4-{(1S)-2-[(4'-fluorobiphenyl-4-yl)oxy]-1-hydroxyethyl}-1,3-thiazol-2-yl)thio]-2-methylpropionic acid tert-butyl ester A (S)-(−)-2-methyl-CBS-oxaborosin (410 mg) and borane-dimethylsulfide complex (1 mol/L methylene chloride solution) (11.84 mL) was dissolved in methylene chloride (30 mL), a solution of the ketone compound (7.21 g) obtained in Example 2-1 in methylene chloride (20 mL) was added dropwise at room temperature over 35 min, and the mixture was stirred for 3 hr 25 min. 1 mol/L Aqueous hydrochloric acid (50 mL) was added by small portions, the mixture was stirred for 1 hr, and the reaction mixture was partitioned, and washed successively with 1 mol/L aqueous hydrochloric acid and saturated brine (each 50 mL). The mixture was dried over anhydrous sodium sulfate, the solvent was evaporated, and the residue was dissolved again in tetrahydrofuran (50 mL). 10% Aqueous potassium carbonate solution (50 mL) was added and the mixture was stirred for 1 hr, extracted with ethyl acetate (100 mL and 50 mL), washed with saturated brine, and dried over anhydrous sodium sulfate. The solvent was evaporated, and the residue was purified by column chromatography (divided in 2 times. Moritex Corporation purif Pack™ Si 60 μm, size 200 was used. eluent: hexane/ethyl acetate=90/10-50/50) to give the title compound (5.80 g).
¹H-NMR (CDCl₃, 300 MHz)
δ: 1.43 (9H, s), 1.64 (6H, s), 2.99 (1H, d, J=4.5 Hz), 4.19 (1H, dd, J=7.5 Hz, 9.6 Hz), 4.42 (1H, d, J=3.9 Hz, 9.6 Hz), 5.25 (1H, m), 6.99 (2H, d, J=6.6 Hz), 7.10 (2H, t, J=6.9 Hz), 7.42-7.51 (5H, m).

Example 10-3

2-[(4-{(1S)-2-[(4'-fluorobiphenyl-4-yl)oxy]-1-hydroxyethyl}-1,3-thiazol-2-yl)thio]-2-methylpropionic acid 2-[(4-{(1S)-2-[(4'-Fluorobiphenyl-4-yl)oxy]-1-hydroxyethyl}-1,3-thiazol-2-yl)thio]-2-methylpropionic acid tert-butyl ester (904 mg) obtained in Example 10-2 was dissolved in dioxane (5 mL), concentrated hydrochloric acid (0.5 mL) was added, and the mixture was stirred at an oil bath temperature of 95° C. for 3 hr 30 min. The reaction mixture was allowed to cool, aqueous potassium hydroxide solution (1 mol/L, 15 mL) was added and the mixture was stirred. This was washed with a mixed solvent (2/1) of hexane and tetrahydrofuran. The aqueous layer was adjusted to about pH 1 with 1 mol/L aqueous hydrochloric acid, extracted with ethyl acetate (100 mL), washed with saturated brine, and dried over anhydrous sodium sulfate. The solvent was evaporated, and the residue was purified by column chromatography (Yamazen HI-FLASH™ COLUMN size 3 L, elution solvent: hexane/ethyl acetate=70/30-0/100) to give the object carboxylic acid as a crude product (624 mg). A similar reaction was repeated for an alcohol compound (4.89 g) to give the object carboxylic acid as a crude product (3.68 g). The obtained carboxylic acid (4.33 g) was dissolved in a mixed solvent of hexane (60 mL) and ethyl acetate (50 mL), (R)-phenethylamine (1.27 mL) was added and the mixture was left standing overnight. The precipitated solid (isomer mixing ratio 73.46:26.54, isomer mixing ratio was determined by analysis using Chiralpak AD-H (4.6×250 mm, elution solvent: hexane/isopropyl alcohol/trifluoroacetic acid=70/30/0.1) manufactured by Daicel) was filtered off, and the solvent of the filtrate was evaporated (isomer mixing ratio 99.4:0.6). The residue was dissolved again in a mixed solvent of hexane (30 mL) and ethyl acetate (20 mL) with heating, hexane (10 mL) was further added and the mixture was left standing at room temperature overnight. The precipitated solid was collected by filtration to give a salt (3.137 g) (isomer ratio 99.79:0.21).

The salt obtained in the above-mentioned resolution step was dissolved in a mixed solvent of water (30 mL) and ethanol (10 mL), and the mixture was adjusted to about pH 1 with 1 mol/L aqueous hydrochloric acid. The solvent was evaporated, and the mixture was extracted with ethyl acetate (100 mL), washed with saturated brine and dried over anhydrous sodium sulfate. The solvent was evaporated, and the residue was purified by column chromatography (Yamazen HI-FLASH™ COLUMN size L, elution solvent: hexane/ethyl acetate=70/30-0/100) to give carboxylic acid (2.19 g, recovery rate from before conversion to salt 50.5%). Therefrom 486 mg was taken and dissolved in hexane (10 mL) and ethyl acetate (4 mL) with heating, and the mixture was allowed to cool. The precipitated crystals were collected by filtration to give the object carboxylic acid as white crystals (357 mg, recovery rate 73.5%). Similarly, the remaining carboxylic acid was processed to give white crystals (1.235 g, recovery rate 74.1%). The crystals obtained in 2 times were combined and recrystallized from hexane (35 mL) and ethyl acetate (20 mL) to give the title compound (1.305 g). The absolute structure was determined to be an S form, since the symbols of the specific optical rotation matched with those of the compound obtained by the method of Example 12.

$^1$H-NMR (DMSO-$d_6$, 300 MHz)

δ: 1.62 (3H, s), 1.64 (3H, s), 4.24 (1H, dd, J=6.9 Hz, 9.6 Hz), 4.39 (1H, dd, J=3.6 Hz, 9.6 Hz), 5.27 (1H, m), 6.98 (2H, d, J=9.0 Hz), 7.10 (2H, t, J=9.0 Hz), 7.44-7.51 (5H, m).

LC-MS: 434 (M+H)$^+$ optical rotation: $[\alpha]_D^{20}$=+51.0° (0.058 g, ethanol, 10 mL, 100 mm)

optical purity: not less than 99.8% ee [Chiralpak AD-H (4.6×250 mm), elution solvent: hexane/isopropyl alcohol/trifluoroacetic acid=70/30/0.1, detection wavelength 260 nm]

Example 11

2-[(4-{(1R)-2-[(4'-fluorobiphenyl-4-yl)oxy]-1-hydroxyethyl}-1,3-thiazol-2-yl)thio]-2-methylpropionic acid By a reaction similar to that in Example 10 and using (R)-(+)-2-methyl-CBS-oxaborosin instead of (S)-(−)-2-methyl-CBS-oxaborosin, the title compound (791 mg) was obtained.

$^1$H-NMR (DMSO-$d_6$, 300 MHz)

δ: 1.62 (3H, s), 1.64 (3H, s), 4.24 (1H, dd, J=6.6 Hz, 9.6 Hz), 4.39 (1H, dd, J=3.6 Hz, 9.6 Hz), 5.27 (1H, m), 6.98 (2H, d, J=8.7 Hz), 7.10 (2H, t, J=8.4 Hz), 7.44-7.51 (5H, m).

LC-MS: 434 (M+H)$^+$ optical rotation: $[\alpha]_D^{20}$=−51.0° (0.044 g, ethanol, 10 mL, 100 mm)

optical purity: 99.8% [Chiralpak AD-H (4.6×250 mm), elution solvent: hexane/isopropyl alcohol/trifluoroacetic acid=70/30/0.1, detection wavelength 260 nm]

(R)-(+)-2-methyl-CBS-oxaborosin instead of (S)-(−)-2-methyl-CBS-oxaborosin, the title compound (791 mg) was obtained.

$^1$H-NMR (DMSO-$d_6$, 300 MHz)

δ: 1.62 (3H, s), 1.64 (3H, s), 4.24 (1H, dd, J=6.6 Hz, 9.6 Hz), 4.39 (1H, dd, J=3.6 Hz, 9.6 Hz), 5.27 (1H, m), 6.98 (2H, d, J=8.7 Hz), 7.10 (2H, t, J=8.4 Hz), 7.44-7.51 (5H, m).

LC-MS: 434 (M+H)$^+$ optical rotation: $[\alpha]_D^{20}$=−51.0° (0.044 g, ethanol, 10 mL, 100 mm) optical purity: 99.8% [Chiralpak AD-H (4.6×250 mm), elution solvent: hexane/isopropyl alcohol/trifluoroacetic acid=70/30/0.1, detection wavelength 260 nm]

Example 12

2-[(4-{(1S)-2-[(4'-fluorobiphenyl-4-yl)oxy]-1-hydroxyethyl}-1,3-thiazol-2-yl)thio]-2-methylpropionic acid

Example 12-1

1-{2-[(2-tert-butoxy-1,1-dimethyl-2-oxoethyl)thio]-1,3-thiaozol-4-yl}-2-[(4'-fluorobiphenyl-4-yl)oxy]ethyl (2R)-3,3,3-trifluoro-2-methoxy-2-phenylpropionic acid

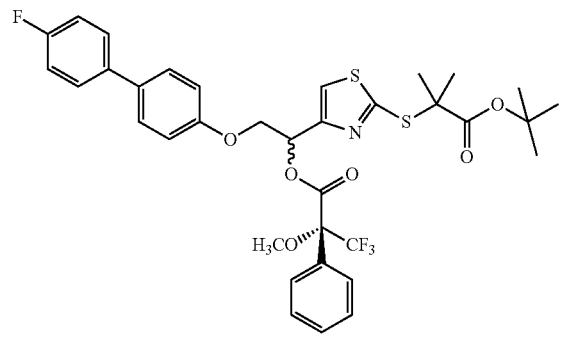 [SMILES: CO[C@@](C(=O)OC(COc1ccc(-c2ccc(F)cc2)cc1)c1csc(SC(C)(C)C(=O)OC(C)(C)C)n1)(c1ccccc1)C(F)(F)F]

2-[(4-{2-[(4'-Fluorobiphenyl-4-yl)oxy]-1-hydroxyethyl}-1,3-thiazol-2-yl)thio]-2-methylpropionic acid tert-butyl ester (2.32 g) obtained by successively performing Examples 2-1, 2-2 was dissolved in pyridine (20 mL), (S)-(+)-α-methoxy-α-trifluoromethylphenylacetyl chloride (1.8 g, 7.13 mmol) and 4-dimethylaminopyridine (1.16 g, 9.5 mmol) were added and the mixture was stirred at room temperature for 30 min. Water (50 mL) was added, and the mixture was extracted with ethyl acetate (100 mL), washed with 1N aqueous hydrochloric acid (20 mL) twice, and with saturated aqueous sodium hydrogen carbonate and saturated brine (each 40 mL), and dried over anhydrous sodium sulfate. The solvent was evaporated and the obtained residue was purified by column chromatography (column: Moritex purif-pack SI 60, 200 g; elution solvent: hexane/ethyl acetate=4/1→6/4) to give a diastereomer mixture (3.29 g). This was recrystallized from hexane (50 mL) to give crystal A (1.179 g). Then, the filtrate was concentrated and the obtained residue was recrystallized from hexane (40 mL) to give crystal B (0.845 g). The absolute configuration of crystal B was found to be (1R) isomer by X ray crystal structure analysis. Therefore, the absolute configuration of crystal A was determined to be (1S) isomer.

$^1$H-NMR (CDCl$_3$, 300 MHz)

crystal A

δ: 1.42 (9H, s), 1.59 (3H, s), 1.60 (3H, s), 3.50 (3H, s), 4.42-4.55 (2H, m), 6.59 (1H, m), 6.90 (2H, d, J=8.7 Hz), 7.07 (2H, t, J=8.7 Hz), 7.34-7.55 (10H, m).

LC-MS: 706 (M$^+$+1)

crystal B

δ: 1.41 (9H, s), 1.58 (3H, s), 1.62 (3H, s), 3.62 (3H, s), 4.41-4.59 (2H, m), 6.62 (1H, m), 6.97 (2H, d, J=8.7 Hz), 7.07-7.13 (3H, m), 7.45-7.58 (9H, m).

Example 12-2

2-[(4-{(1S)-2-[(4'-fluorobiphenyl-4-yl)oxy]-1-hydroxyethyl}-1,3-thiazol-2-yl)thio]-2-methylpropionic acid Crystal A (900 mg) obtained in Example 12-1 was dissolved in tetrahydrofuran (10 mL), 1 mol/L aqueous sodium hydroxide solution (1.9 mL) was added and the mixture was heated under reflux for 2 hr 10 min. Since the acyl compound (starting material) was found remaining therein by TLC, aqueous sodium hydroxide solution (0.6 mL) was added, and the mixture was further heated under reflux for 7 hr 30 min. The mixture was allowed to cool, water (10 mL) was added, and the mixture was extracted with diethyl ether (20 mL), washed successively with saturated aqueous sodium hydrogen carbonate and saturated brine, and dried over anhydrous sodium sulfate. The solvent was evaporated and the obtained residue was purified by column chromatography (column: Moritex purif-pack SI 60, 60 g; elution solvent: hexane/ethyl acetate=4/1→6/4) to give an alcohol compound (623 mg). This (581 mg) was dissolved in methylene chloride (1 mL), trifluoroacetic acid (1 mL) was added and the mixture was stirred overnight. The solvent was evaporated, and the residue was purified by column chromatography (column: Moritex purif-pack SI 30, 60 g; elution solvent: hexane/ethyl acetate=6/4→ethyl acetate alone) to give the title compound (311 mg).

$^1$H-NMR (CDCl$_3$, 300 MHz)

δ: 1.62 (3H, s), 1.64 (3H, s), 4.23 (1H, dd, J=6.8 Hz, 9.6 Hz), 4.40 (1H, dd, J=3.72 Hz, 9.6 Hz), 5.27 (1H, m), 6.98 (2H, d, J=8.8 Hz), 7.10 (2H, t, J=8.8 Hz), 7.43-7.50 (5H, m).

LC-MS: 434 (M+H)$^+$ optical rotation: $[\alpha]^{21.8}_D$+47.75 (c 1.00, EtOH)

Example 13

2-[(4-{(1R)-2-[(4'-fluorobiphenyl-4-yl)oxy]-1-hydroxyethyl}-1,3-thiazol-2-yl)thio]-2-methylpropionic acid In the same manner as in Example 12-2 and using crystal B (800 mg) obtained in Example 12-1, the title compound (310 mg) was obtained.

$^1$H-NMR (CDCl$_3$, 300 MHz)

δ: 1.61 (3H, s), 1.64 (3H, s), 4.24 (1H, dd, J=6.8 Hz, 9.6 Hz), 4.40 (1H, dd, J=3.72 Hz, 9.6 Hz), 5.27 (1H, m), 6.98 (2H, d, J=8.8 Hz), 7.11 (2H, t, J=8.8 Hz), 7.43-7.50 (5H, m).

LC-MS: 434 (M+H)

optical rotation $[\alpha]^{22.3}_D$−51.07 (c 1.00, EtOH)

Experimental Example 1

Transactivation Test for Human Peroxisome Proliferator-Activated Receptor (PPAR)$_\alpha$ CV-1 cells (CCL-70, manufactured by Dainippon Pharma Co., Ltd.) cultured in Dulbecco's Modified Eagle Medium (DMEM) containing 10% fetal bovine serum (FBS) were transfected, using Lipofectamine 2000 (manufactured by Invitrogen), with pBIND vector (manufactured by Promega) that expresses a fusion protein of a DNA binding region of a yeast transcription factor (GAL4) and a human PPARα ligand binding region (GAL4-hPPARαLBD, manufactured based on Diabetes 47: 1841-1847, 1998), and an internal standard renilla luciferase, and GAL4 responsive TK vector that expresses reporter firefly luciferase (manufactured by Promega). 24 hr later, the medium was changed to a serum free medium containing a test compound, and the luciferase activity after 24 hr was measured.

The results are shown in Table 1.

TABLE 1

| Example | transactivation action (EC50, nmol/l) |
|---|---|
| 2 | 8.4 |
| 3 | 4.7 |
| 12 | 3.1 |
| compound A | 10.41 |

Compound A: 2-[(4-{2-[(4'-fluorobiphenyl-4-yl)oxy]ethyl}-1,3-thiazol-2-yl)thio]-2-methylpropionic acid The results reveal that the compound of the present invention has a strong transcription activating action on human PPAR$_\alpha$.

From the above, it has been clarified that the compound of the present invention has a human PPARα agonist action.

As shown in the above Table, in this Experimental Example, the transcription activation action of compound A was 10.41 nmol/l, and the preferable compounds of the present invention, particularly the compound of Example 12 showed 3 times or more stronger activity.

Experimental Example 2

Lipid-Lowering Action In Vivo

1) Blood Triglyceride (TG)-Lowering Action in Normal Rats 7 to 9-week-old male SD rats (manufactured by SEAC Yoshitomi, Ltd.) were used for the test. A test compound and a control compound (GW-9578: J. Med. Chem. 1999, 42, 3785-3788) were dissolved or suspended in 1% ethanol, 0.05% Tween80 (final concentration), and 0.5% hydroxypropylmethyl cellulose (HPMC) was added to adjust to a given concentration. The prepared solution was orally administered once a day for 4 days. After administration for 4 days, blood samples were collected from the jugular vein under nonfasting condition and blood TG was measured by an enzyme method. The lowering rate was calculated by determining the rate of a value obtained by subtracting the average blood TG of a drug administration group from the average blood TG of a vehicle administration group, to the average blood TG of the vehicle administration group.

The results are shown in Table 2.

TABLE 2

| Example | TG lowering rate |
|---|---|
| GW-9578 | 50-60 (%, 0.3 mg/kg, p.o.) |
| 2 | 56 (%, 0.3 mg/kg, p.o.) |
| 12 | 52 (%, 0.1 mg/kg, p.o.) |

The results reveal that the compound of the present invention has a superior blood hypotriglyceridemic action.

The compound of Example 12 showed 15.1% of TG-lowering action by administration at 0.01 mg/kg, whereas compound A scarcely showed a TG-lowering action at the same dose (TG-lowering action: 0.7%). Therefore, the compound of Experimental Example 12 was found show a superior TG-lowering action from a low dose, as compared to compound A.

2) Influence on Serum Lipid of High Cholesterol Diet-Treated Rat 8-week-old male SD rats (manufactured by SEAC Yoshitomi, Ltd.) were raised on a standard diet CE-2 (manufactured by Japan Clea, Inc.) added with 1% cholesterol, 2% olive oil and 0.2% cholic acid, from one week before test compound administration to the last day of the administration. A test compound and a control compound (GW-9578) were dissolved or suspended in 1% ethanol and 0.05% Tween80 (final concentration), and 0.5% hydroxypropylmethyl cellulose (HPMC) was added to adjust to a given concentration. The prepared solution was orally administered once a day for 5 days. After administration for 5 days, blood samples were collected from the jugular vein under non-fasting condition and blood lipid was measured by an enzyme method. The lowering rate was calculated by determining the rate of a value obtained by subtracting the average blood TG (or average blood TC) of a drug administration group from the average blood triglyceride (TG) (or average blood total cholesterol (TC)) of a vehicle administration group, to the average blood TG (or average blood TC) of the vehicle administration group.

The results are shown in Table 3.

TABLE 3

| | TG lowering rate (%, 0.3 mg/kg, p.o.) | |
|---|---|---|
| Example | TG | TG |
| GW-9578 | 30-50 | 30-50 |
| 2 | 38 | 34 |

The results reveal that the compound of the present invention has a superior blood hypolipidemic (TG, TC) action.

From the above results, it has been clarified that the compound of the present invention has a superior hypolipidemic action.

Experimental Example 3

Metabolizing Isoform Identification Test (Oxidative Metabolism by Microsome)

As a reaction mixture for the CYP isoform identification, a reaction mixture containing microsome [$^{14}$C-labeled test compound (2 μmol/L), microsome (human liver microsome at 0.5 mg protein/mL or microsome expressing CYP at 50 pmol CYP/mL (Control microsome, CYP1A2, CYP2A6, CYP2B6, CYP2C8, CYP2C9, CYP2C19, CYP2D6, CYP2E1 or CYP3A4)), EDTA (0.05 mmol/L) and Na—K phosphate buffer (pH 7.4, 0.1 mol/L)] was prepared and, after preincubation at 37° C. for 5 min, a solution of the NADPH generating system [β-NADP+ (0.5 mmol/L), glucose-6-phosphate (G-6-P) (5.0 mmol/L), magnesium chloride (5.0 mmol/L) and G-6-P DH (1.0 unit/mL)] was added to start the reaction. For CYP expressing microsomes for CYP2A6 and CYP2C9, Tris-HCl buffer (pH 7.4, 0.1 mol/L) was used instead of Na—K phosphate buffer (pH 7.4, 0.1 mol/L).

On the other hand, as a reaction mixture for studying inhibitors, [$^{14}$C-labeled test compound (0.2 μmol/L and 2 μmol/L), inhibitor solution (Sulfaphenazole) (10 μmol/L), human liver microsome (0.5 mg protein/mL), EDTA (0.05 mmol/L) and Na—K phosphate buffer (pH 7.4, 0.1 mol/L)] was prepared and, after preincubation at 37° C. for 5 min, a solution of the NADPH generating system was added thereto to start the reaction.

These reaction mixtures were incubated at 37° C. for 20 min, and a 3-fold amount of ethanol was added to the reaction mixtures to terminate the reaction. To the reaction mixture was added a predetermined amount of an unlabeled metabolite mixed solution, and the mixture was stirred (about 5 min), centrifuged (4° C., 3000 rpm, 10 min) and the supernatant was collected. To the residue was added a 3-fold amount of ethanol relative to the reaction mixture, and the mixture was stirred (about 5 min), and centrifuged (4° C., 3000 rpm, 10 min). The supernatant was collected and combined with the supernatant collected earlier, and the solvent was evaporated under a nitrogen stream at about 40° C. To the residue was added a predetermined amount of HPLC mobile phase or suitable solvent, and the mixture was stirred and used as an HPLC sample. The sample was injected into HPLC and a radiochromatogram was obtained. From the obtained radiochromatogram, the metabolism activity and metabolite generating activity of the $^{14}$C-labeled test compound was calculated.

As a result, it was clarified that compound A is mainly metabolized by CYP2C9, and also metabolized by CYP3A4, CYP2C8 and CYP2C19. In contrast, oxidative metabolism of the compound of Example 12 by human liver microsome could not be confirmed.

Since oxidative metabolism of compound A was observed in human liver microsome, investigation using an inhibitor was performed. From the investigation using the inhibitor, it was also confirmed that the enzyme mainly involved in the metabolism of compound A was CYP2C9.

INDUSTRIAL APPLICABILITY

According to the present invention, a highly safe compound having a PPARα agonist action and useful as a drug for the prophylaxis and/or treatment of hyperlipidemia can be provided. According to the present invention, moreover, an intermediate useful for synthesizing the above-mentioned compound can be provided.

This application is based on a patent application No. 2008-306803 filed in Japan (filing date: Dec. 1, 2008), the contents of which are incorporated in full herein.

The invention claimed is:

1. A carboxylic acid derivative containing a thiazole ring represented by the following formula (I)

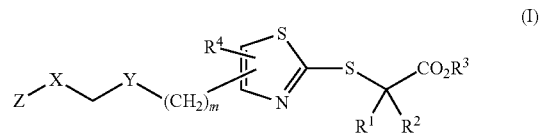

wherein
R$^1$ and R$^2$ are the same or different and each is a hydrogen atom or an alkyl group optionally having substituent(s), or R$^1$ and R$^2$ are bonded to each other to form a cycloalkyl group optionally having substituent(s);
R$^3$ is a hydrogen atom or an alkyl group optionally having substituent(s);
R$^4$ is a hydrogen atom, an alkyl group optionally having substituent(s) or an aryl group optionally having substituent(s);
m is an integer of 0 to 3;
X is a bond, an oxygen atom or a sulfur atom;
Y is a carbonyl group or a group represented by —CH(OR$^5$)— wherein R$^5$ is a hydrogen atom or an alkyl group optionally having substituent(s); and Z is
a halogen atom,
an alkyl group optionally having substituent(s),
a cycloalkyl group optionally having substituent(s),
an aryl group optionally having substituent(s),
an arylalkyl group optionally having substituent(s),
an arylalkenyl group optionally having substituent(s),
an aryloxyalkyl group optionally having substituent(s),
a heteroaryl group optionally having substituent(s) or
a heteroarylalkyl group optionally having substituent(s), or a pharmaceutically acceptable salt thereof.

2. The carboxylic acid derivative according to claim 1, which is represented by the following formula (I')

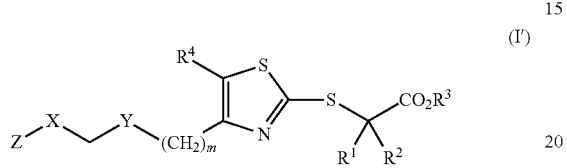

(I')

wherein $R^1$, $R^2$, $R^3$, $R^4$, m, X, Y and Z are as defined above, or a pharmaceutically acceptable salt thereof.

3. The carboxylic acid derivative according to claim 1, wherein $R^1$ and $R^2$ are the same or different and each is a $C_{1-15}$ alkyl group,
$R^3$ is a hydrogen atom or a $C_{1-15}$ alkyl group;
$R^4$ is a hydrogen atom;
m is 0;
X is a bond or an oxygen atom;
Y is a carbonyl group or a group represented by —CH(OR$^5$)— wherein $R^5$ is a hydrogen atom or a $C_{1-15}$ alkyl group; and
Z is a halogen atom, a $C_{1-15}$ alkyl group, a $C_{6-14}$ aryl group optionally having substituent(s) or a heteroaryl group optionally having substituent(s),
or a pharmaceutically acceptable salt thereof.

4. The carboxylic acid derivative according to claim 1, wherein $R^1$ and $R^2$ are the same or different and each is a $C_{1-6}$ alkyl group,
$R^3$ is a hydrogen atom or a $C_{1-6}$ alkyl group;
$R^4$ is a hydrogen atom;
m is 0;
X is a bond or an oxygen atom;
Y is a carbonyl group or a group represented by —CH(OR$^5$)— wherein $R^5$ is a hydrogen atom or a $C_{1-6}$ alkyl group; and
Z is
(1) a halogen atom,
(2) a $C_{1-6}$ alkyl group,
(3) a $C_{6-14}$ aryl group optionally having 1 to 3 substituents selected from the group consisting of
   (i) $C_{1-6}$ alkyl,
   (ii) halo-$C_{1-6}$ alkyl,
   (iii) $C_{6-14}$ aryl and
   (iv) halo-$C_{6-14}$ aryl
or
(4) a heteroaryl group optionally having 1 to 3 substituents selected from the group consisting of
   (i) $C_{1-6}$ alkyl,
   (ii) halo-$C_{1-6}$ alkyl,
   (iii) $C_{6-14}$ aryl and
   (iv) halo-$C_{6-14}$ aryl,
or a pharmaceutically acceptable salt thereof.

5. The carboxylic acid derivative according to claim 1, wherein, in the formula (I), an aryl group optionally having substituent(s) or a heteroaryl group optionally having substituent(s) for Z is represented by a substituent selected from the group consisting of the following formulas (Za-Zn)

(Za)

(Zb)

(Zc)

(Zd)

(Ze)

(Zf)

(Zg)

(Zh)

(Zi)

(Zj)

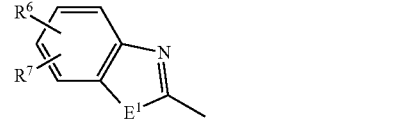

(Zk)

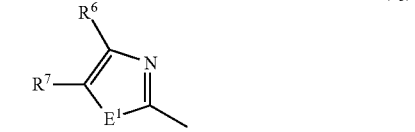

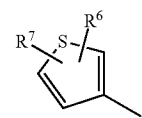

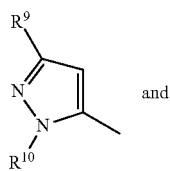

and

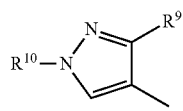

wherein
$R^6$, $R^7$, $R^8$, $R^9$ and $R^{10}$ are the same or different and each is a hydrogen atom, a $C_{1-6}$ alkyl group, a halo-$C_{1-6}$ alkyl group, a $C_{6-14}$ aryl group or a halo-$C_{6-14}$ aryl group, and $E^1$ is an oxygen atom, a sulfur atom or —$NR^{20}$— wherein $R^{20}$ is a hydrogen atom, a $C_{1-6}$ alkyl group, a $C_{3-7}$ cycloalkyl group, a $C_{6-14}$ aryl group, a $C_{6-14}$ aryl-$C_{1-6}$ alkyl group or a heteroaryl-$C_{1-6}$ alkyl group, or a pharmaceutically acceptable salt thereof.

6. A carboxylic acid which is 2-[(4-{[(4'-fluorobiphenyl-4-yl)oxy]acetyl}-1,3-thiazol-2-yl)thio]-2-methylpropionic acid;

2-[(4-{2-[(4'-fluorobiphenyl-4-yl)oxy]-1-hydroxyethyl}-1,3-thiazol-2-yl)thio]-2-methylpropionic acid;

2-[(4-{[(4'-chlorobiphenyl-4-yl)oxy]acetyl}-1,3-thiazol-2-yl)thio]-2-methylpropionic acid;

2-[(4-{2-[(4'-chlorobiphenyl-4-yl)oxy]-1-hydroxyethyl}-1,3-thiazol-2-yl)thio]-2-methylpropionic acid;

2-[(4-{2-[(4'-fluorobiphenyl-4-yl)oxy]-1-methoxyethyl}-1,3-thiazol-2-yl)thio]-2-methylpropionic acid;

2-{[4-(2-{[5-(4-fluorophenyl)pyridin-2-yl]oxy}-1-hydroxyethyl)-1,3-thiazol-2-yl]thio}-2-methylpropionic acid;

2-[(4-{(1S)-2-[(4'-fluorobiphenyl-4-yl)oxy]-1-hydroxyethyl}-1,3-thiazol-2-yl)thio]-2-methylpropionic acid;
or
2-[(4-{(1R)-2-[(4'-fluorobiphenyl-4-yl)oxy]-1-hydroxyethyl}-1,3-thiazol-2-yl)thio]-2-methylpropionic acid;

or a derivative thereof or a pharmaceutically acceptable salt thereof.

7. A pharmaceutical composition comprising the carboxylic acid derivative according to claim 1 or a pharmaceutically acceptable salt thereof, and a pharmaceutically acceptable carrier.

8. A method for the treatment of a disease selected from hyperlipidemia, hyperlipidemia secondary to diabetes, arteriosclerosis, ischemic cardiac diseases and diabetes, comprising administering the carboxylic acid derivative according to claim 1 or a pharmaceutically acceptable salt thereof to a subject in need thereof.

* * * * *

UNITED STATES PATENT AND TRADEMARK OFFICE
CERTIFICATE OF CORRECTION

PATENT NO.        : 8,497,382 B2
APPLICATION NO.   : 13/132292
DATED             : July 30, 2013
INVENTOR(S)       : Naoko Ando Page 1 of 1

It is certified that error appears in the above-identified patent and that said Letters Patent is hereby corrected as shown below:

IN THE CLAIMS:

Claim 6, at column 48, line 18, delete "or a derivative thereof".

Signed and Sealed this
Eighth Day of July, 2014

Michelle K. Lee
*Deputy Director of the United States Patent and Trademark Office*